US009549901B2

(12) United States Patent
Shi et al.

(10) Patent No.: US 9,549,901 B2
(45) Date of Patent: Jan. 24, 2017

(54) LIPID-POLYMER HYBRID PARTICLES

(75) Inventors: Jinjun Shi, Boston, MA (US); Zeyu Xiao, Boston, MA (US); Cristian Vilos, Newton, MA (US); Alexander Votruba, Boston, MA (US); Robert S. Langer, Newton, MA (US); Omid C. Farokhzad, Chestnut Hill, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 863 days.

(21) Appl. No.: 13/820,351

(22) PCT Filed: Sep. 2, 2011

(86) PCT No.: PCT/US2011/050334
§ 371 (c)(1),
(2), (4) Date: Aug. 15, 2013

(87) PCT Pub. No.: WO2012/031205
PCT Pub. Date: Mar. 8, 2012

(65) Prior Publication Data
US 2013/0315831 A1    Nov. 28, 2013

Related U.S. Application Data

(60) Provisional application No. 61/380,095, filed on Sep. 3, 2010.

(51) Int. Cl.
| | | |
|---|---|---|
| *A61K 9/16* | (2006.01) |
| *A61K 9/50* | (2006.01) |
| *A61K 31/337* | (2006.01) |
| *A61K 31/704* | (2006.01) |
| *A61K 31/713* | (2006.01) |
| *A61K 49/00* | (2006.01) |
| *A61K 9/127* | (2006.01) |
| *A61K 9/51* | (2006.01) |
| *C12N 15/11* | (2006.01) |
| *A61K 39/39* | (2006.01) |
| *A61K 9/00* | (2006.01) |
| *A61K 39/00* | (2006.01) |

(52) U.S. Cl.
CPC ........... *A61K 9/5073* (2013.01); *A61K 9/1271* (2013.01); *A61K 9/5123* (2013.01); *A61K 31/337* (2013.01); *A61K 31/704* (2013.01); *A61K 31/713* (2013.01); *A61K 39/39* (2013.01); *A61K 49/0002* (2013.01); *C12N 15/111* (2013.01); *A61K 9/0019* (2013.01); *A61K 2039/55511* (2013.01); *A61K 2039/55555* (2013.01); *A61K 2039/55561* (2013.01); *C12N 2310/14* (2013.01); *C12N 2310/16* (2013.01); *C12N 2320/32* (2013.01)

(58) Field of Classification Search
CPC ...... A61K 9/51; A61K 9/1075; A61K 9/5153; A61K 9/127; A61K 9/1272; A61K 9/1271; A61K 9/1273; A61K 9/1274; A61K 9/1277
USPC .............. 424/9.1, 9.321, 417, 418, 493, 500
See application file for complete search history.

(56) References Cited

U.S. PATENT DOCUMENTS

| | | | |
|---|---|---|---|
| 4,638,045 A | 1/1987 | Kohn et al. |
| 4,806,621 A | 2/1989 | Kohn et al. |
| 4,946,929 A | 8/1990 | D'Amore et al. |
| 5,010,167 A | 4/1991 | Ron et al. |
| 5,019,379 A | 5/1991 | Domb et al. |
| 5,399,665 A | 3/1995 | Barrera et al. |
| 5,512,600 A | 4/1996 | Mikos et al. |
| 5,514,378 A | 5/1996 | Mikos et al. |
| 5,696,175 A | 12/1997 | Mikos et al. |
| 5,716,404 A | 2/1998 | Vacanti et al. |
| 5,736,372 A | 4/1998 | Vacanti et al. |
| 5,770,417 A | 6/1998 | Vacanti et al. |
| 5,804,178 A | 9/1998 | Vacanti et al. |
| 5,837,752 A | 11/1998 | Shastri et al. |
| 5,902,599 A | 5/1999 | Anseth et al. |
| 6,095,148 A | 8/2000 | Shastri et al. |
| 6,123,727 A | 9/2000 | Vacanti et al. |
| 6,506,577 B1 | 1/2003 | Deming et al. |
| 6,632,922 B1 | 10/2003 | Deming et al. |
| 6,686,446 B2 | 2/2004 | Deming et al. |
| 6,818,732 B2 | 11/2004 | Deming et al. |
| 2003/0099668 A1 | 5/2003 | Bachmann et al. |
| 2003/0143184 A1* | 7/2003 | Seo ...................... A61K 31/337 424/78.17 |
| 2003/0219384 A1* | 11/2003 | Donath ................ A61K 9/5026 424/9.6 |
| 2004/0115254 A1 | 6/2004 | Niedzinski et al. |
| 2004/0115433 A1 | 6/2004 | Elaissari et al. |

(Continued)

FOREIGN PATENT DOCUMENTS

| | | |
|---|---|---|
| WO | WO 03/024481 | 3/2003 |
| WO | WO 2008/124632 | 10/2008 |

(Continued)

OTHER PUBLICATIONS

International Preliminary Report on Patentability for International Application No. PCT/US/2011/050334 dated Mar. 13, 2014, 8 pages.

(Continued)

*Primary Examiner* — Micah-Paul Young
(74) *Attorney, Agent, or Firm* — Fish & Richardson P.C.

(57) ABSTRACT

A particle includes an aqueous core; a first amphiphilic layer surrounding the aqueous core; and a polymeric matrix surrounding the first amphiphilic layer.

33 Claims, 10 Drawing Sheets

(56) References Cited

U.S. PATENT DOCUMENTS

| | | | |
|---|---|---|---|
| 2005/0115254 A1* | 6/2005 | Knight | F24F 3/153 62/176.1 |
| 2006/0057211 A1 | 3/2006 | Chorny et al. | |
| 2008/0081074 A1 | 4/2008 | Gu et al. | |
| 2009/0023673 A1 | 1/2009 | Manoharan et al. | |
| 2009/0061010 A1 | 3/2009 | Zale et al. | |
| 2009/0105172 A1 | 4/2009 | Diener et al. | |
| 2010/0076056 A1 | 3/2010 | Manoharan et al. | |

FOREIGN PATENT DOCUMENTS

| | | |
|---|---|---|
| WO | WO 2009/086558 | 7/2009 |
| WO | WO 2009/088891 | 7/2009 |
| WO | WO 2010/042877 | 4/2010 |
| WO | WO 2010/053572 | 5/2010 |
| WO | WO 2010/062322 | 6/2010 |

OTHER PUBLICATIONS

Akinc et al., "A combinatorial library of lipid-like materials for delivery of RNAi therapeutics," Nat. Biotechnol. 26(5):561-9, 2008.

Akinc et al., "Development of Lipidoid—siRNA Formulations for Systemic Delivery to the Liver," Mol. Ther. 17(5):872-879, 2009.

Allcock and Lampe, "Inorganic Polymers," Contemporary Polymer Chemistry Prentice-Hall 19(3):133-165, 1981.

Anton et al., "Design and production of nanoparticles formulated from nano-emulsion templates—A review," J. Control Release 128(3):185-199, 2008.

Awasthi et al., "The Non-ABC Drug Transporter RLIP76 (RALBP-1) Plays a Major Role in the Mechanisms of Drug Resistance," Curr. Drug Metab. 8(4):315-323, 2007.

Beaucage and Caruthers, "Deoxynucleoside phosphoramidites—A new class of key intermediates for deoxypolynucleotide synthesis," Tetrahedron Lett. 22(20):1859-1862, 1981.

Cohen et al., "CD4+ T-Cells from Mice Immunized to Syngeneic Sarcomas Recognize Distinct, Non-Shared Tumor Antigens," Cancer Res. 54(4):1055-1058, 1994.

Cotten et al., "Receptor-Mediated Transport of DNA into Eukaryotic Cells," Methods Enzymol. 217:618-644, 1993.

Debbage and Jaschke, "Molecular imaging with nanoparticles: giant roles for dwarf actors," Histochem. Cell Biol. 130(5):845-875, 2008.

De Clercq, "Interferon induction by polynucleotides, modified polynucleotides, and polycarboxylates," Methods Enzymol. 78(Pt A):227-236, 1981.

Deming et al., "Facile synthesis of block copolypeptides of defined architecture," Nature 390(6658):386-389, 1997.

Dong and Mumper, "Nanomedicinal strategies to treat multidrug-resistant tumors: current progress," Nanomedicine (London) 5(4):597-615, Jun. 2010.

Fletcher et al., "ABC transporters in cancer: more than just drug efflux pumps," Nat. Rev. Cancer 10(2):147-156, Feb. 2010.

Froehler et al., "Synthesis of DNA via deoxynucleoside H-phosphonate intermediates," Nucleic Acids Res. 11;14(13):5399-5407, 1986.

Fujita et al., "MiR-148a attenuates paclitaxel resistance of hormone-refractory, drug-resistant prostate cancer PC3 cells by regulating MSK1 expression," J. Biol. Chem. 285(25):19076-19084, Jun. 2010.

Gaffney et al., "Large-Scale Oligonucleotide Synthesis by the H-Phosphonate Method," Tetrahedron Lett. 29:2619-2622, 1988.

Garegg et al., "Nucleoside H-Phosphonates. III. Chemical Synthesis of Oligodeoxyribonucleotides by the Hydrogenphosphonate Approach," Tetrahedron Lett. 27:4051-4054, 1986.

Garegg et al., "Nucleoside H-Phosphonates. IV. Automated Solid Phase Synthesis of Oligoribonucleotides by the Hydrogenphosphonate Approach," Tetrahedron Lett. 27:4055-4058, 1896.

Garnett, "Targeted drug conjugates: principles and progress," Adv. Drug Deliv. Rev. 53(2):171-216, 2001.

Gref et al., "The controlled intravenous delivery of drugs using PEG-coated sterically stabilized nanospheres," Adv. Drug Deliv. Rev. 16(2-3):215-233, 1995.

Gref et al., "Biodegradable long-circulating polymeric nanospheres," Science 263(5153):1600-1603, 1994.

Gref et al., "'Stealth' corona-core nanoparticles surface modified by polyethylene glycol (PEG): influences of the corona (PEG chain length and surface density) and of the core composition on phagocytic uptake and plasma protein adsorption," Colloids Surf B Biointerfaces 18(3-4):301-313, 2000.

Hamidi et al., "Pharmacokinetic Consequences of Pegylation," Drug Deliv. 13(6):399-409, 2006.

Javier et al., "Aptamer-Targeted Gold Nanoparticles as Molecular-Specific Contrast Agents for Reflectance Imaging," Bioconjug. Chem. 19(6):1309-1312, 2008.

Jia et al., "Mechanisms of drug combinations: interaction and network perspectives," Nat. Rev. Drug Discov. 8(2):111-128, 2009.

Klibanov et al., "Amphipathic polyethyleneglycols effectively prolong the circulation time of liposomes," FEBS Lett. 268(1):235-237, 1990.

Langer, "Selected advances in drug delivery and tissue engineering," J. Control Release 62(1-2):7-11, 1999.

Langer, "Biomaterials in Drug Delivery and Tissue Engineering: One Laboratory's Experience," Acc. Chem Res. 33(2):94-101, 2000.

Latil et al., "VEGF overexpression in clinically localized prostate tumors and neuropilin-1 overexpression in metastatic forms," Int. J. Cancer 89(2):167-171, 2000.

Lee, "Reversing agents for ATP-binding cassette drug transporters," Methods Mol. Biol. 596:325-340, 2010.

Levy, "Induction of interferon in vivo and in vitro by polynucleotides and derivatives, and preparation of derivatives," Methods Enzymol. 78(Pt A):242-251, 1981.

Lim et al., "Cationic hyperbranched poly(amino ester); a novel class of DNA condensing molecule with cationic surface, biodegradable three-dimensional structure, and tertiary amine groups in the interior," J. Am. Chem. Soc. 123(10):2460-2461, 2001.

Love et al., "Lipid-like materials for low-dose, in vivo gene silencing," Proc. Natl. Acad. Sci. U.S.A. 107(5):1864-1869, 2010.

Milowsky et al., "Vascular targeted therapy with anti-prostate-specific membrane antigen monoclonal antibody J591 in advanced solid tumors," J. Clin. Oncol. 25(5):540-547, 2007.

Morris et al., "Phase I evaluation of J591 as a vascular targeting agent in progressive solid tumors," Clin. Cancer Res. 13(9):2707-2713, 2007.

Mundargi et al., "Nano/micro technologies for delivering macromolecular therapeutics using poly(D,L-lactide-co-glycolide) and its derivatives," J. Control Release 125(3):193-209, 2008.

Nakashima et al, "Particle control of emulsion by membrane emulsification and its applications," Adv. Drug Deliv. Rev. 45(1):47-56, 2000.

Pasqualini et al., "Searching for a molecular address in the brain," Mol. Psychiatry1(6):421-422, 1996.

Patel et al., "Rescue of paclitaxel sensitivity by repression of Prohibitin1 in drug-resistant cancer cells," Proc. Natl. Acad. Sci. U.S.A. 107(6):2503-2508, Feb. 2010.

Peer et al., "Nanocarriers as an emerging platform for cancer therapy," Nat. Nanotechnol. 2(12):751-760, 2007.

Rajott et al., "Molecular heterogeneity of the vascular endothelium revealed by in vivo phage display," J. Clin. Invest. 102(2):430-437, 1998.

Sambrook T., et al., Molecular Cloning: A Laboratory Manual, Cold Spring Harbor Laboratory Press, New York, 1989 (Table of Contents Only).

Semple et al., "Rational design of cationic lipids for siRNA delivery," Nat. Biotechnol. 28(2):172-176, Feb. 2010.

Stavrovskaya and Stromskaya, "Transport proteins of the ABC family and multidrug resistance of tumor cells," Biochemistry (Mosc). 73(5):592-604, 2008.

Torchilin, "Drug targeting," Eur. J. Pharm. Sci. 11(Suppl 2):S81-S91, 2000.

(56) References Cited

OTHER PUBLICATIONS

Torrence, "Preparation of a synthetic polynucleotide interferon inducer," Methods Enzymol. 78(Pt A):326-31, 1981.
Uhrich et al., "Polymeric Systems for Controlled Drug Release," Chem. Rev. 99(11):3181-3198, 1999.
Veronese et al., "The Impact of PEGylation on Biological Therapies," BioDrugs 22(5):315-329, 2008.
VertutDoi et al., "Binding and uptake of liposomes containing a poly(ethylene glycol) derivative of cholesterol (stealth liposomes) by the macrophage cell line J774: influence of PEG content and its molecular weight," Biochim. Biophys. Acta 1278(1):19-28, 1996.
Wang et al., "A novel biodegradable gene carrier based on polyphosphoester," J. Am. Chem. Soc. 123(38):9480-9481, 2001.
Xie et al., "Error-prone translesion synthesis mediates acquired chemoresistance," Proc. Natl. Acad. Sci. U.S.A. 107(48):20792-20797, Nov. 2010.
Yamamoto et al., "The discovery of immunostimulatory DNA sequence," Springer Semin. Immunopathol. 22(1-2):11-19, 2000.
Yokoyama et al., "Toxicity and antitumor activity against solid tumors of micelle-forming polymeric anticancer drug and its extremely long circulation in blood," Cancer Res. 51(12):3229-3236, 1991.
Yue et al., "Knocking Down Breast Cancer Resistance Protein (Bcrp) by Adenoviral Vector-Mediated RNA Interference (RNAi) in Sandwich-Cultured Rat Hepatocytes: A Novel Tool to Assess the Contribution of Bcrp to Drug Biliary Excretion," Mol. Pharm. 6(1):134-143, 2009.
Zhou et al., "Substrates and Inhibitors of Human Multidrug Resistance Associated Proteins and the Implications in Drug Development," Curr. Med. Chem. 15(20):1981-2039, 2008.
International Search Report and Written Opinion mailed May 2, 2012 in international application No. PCT/US2011/050334, 13 pgs.

\* cited by examiner

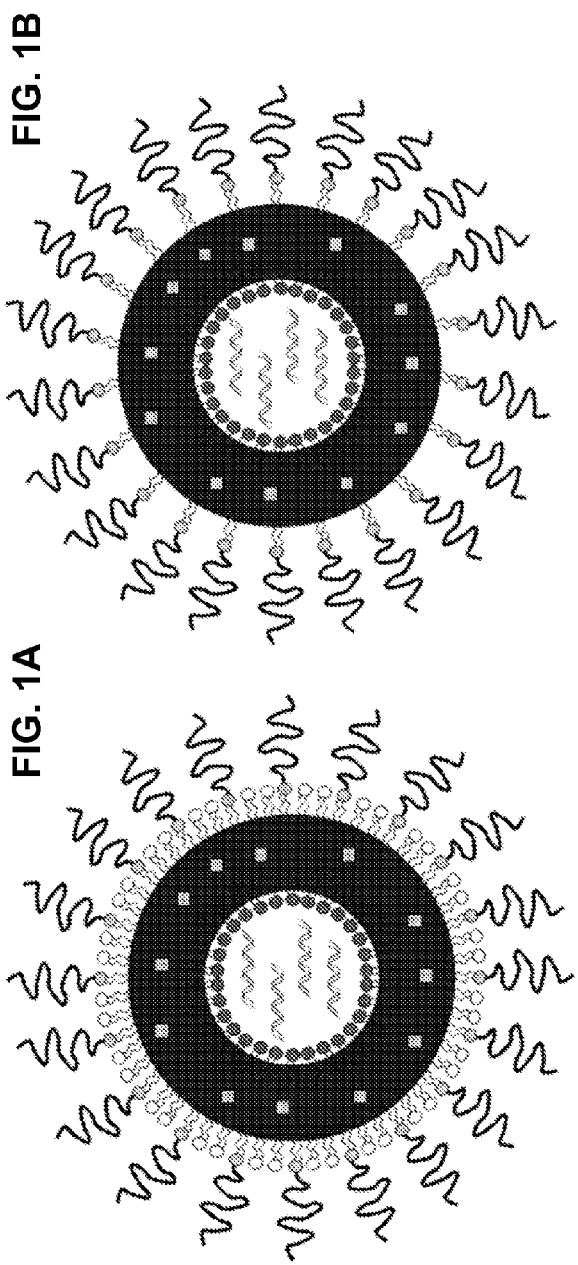
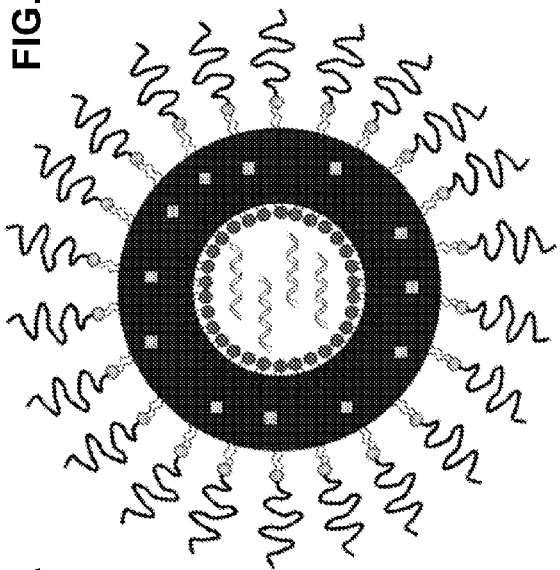
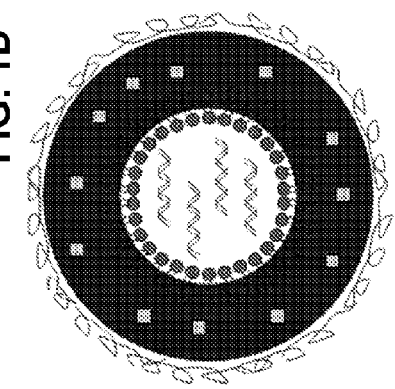
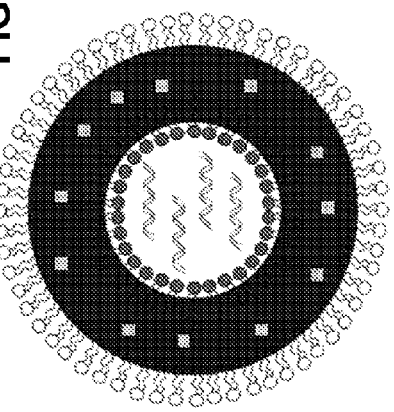
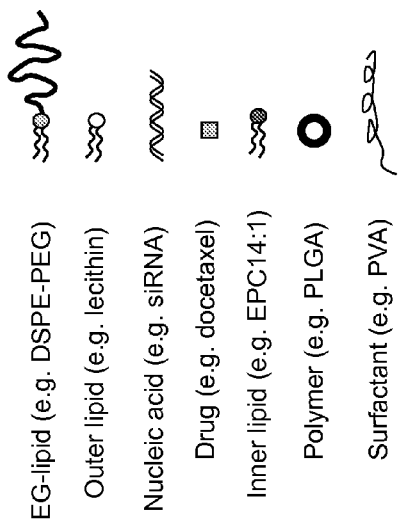
FIG. 1A FIG. 1B FIG. 1C FIG. 1D

LIPID-POLYMER HYBRID PARTICLES

CROSS-REFERENCE TO RELATED APPLICATIONS

This application is a U.S. National Phase Application under 35 U.S.C. §371 of International Patent Application No. PCT/US2011/050334, filed on Sep. 2, 2011, which claims priority to U.S. Provisional Patent Application Ser. No. 61/380,095, filed on Sep. 3, 2010, all of which are incorporated herein by reference in their entireties.

STATEMENT AS TO FEDERALLY SPONSORED RESEARCH

This invention was made with Government support under Grant Nos. CA119349 and EB003647, awarded by the National Institutes of Health. The Government has certain rights in the invention.

TECHNICAL FIELD

This invention relates to particulate compositions that include lipid and polymer components.

BACKGROUND

The medical application of nanotechnology has a significant impact on the economy. In 2004, nanomedicine sales reach 6.8 billion dollars, with over 200 companies and 38 products worldwide. A minimum of 3.8 billion dollars in nanotechnology research and development is being invested every year. The introduction of nanoparticles for the treatment and detection of major human diseases is expected to result in the explosion of the market for this class of biomaterials. The value of a platform by which nanoparticles may be developed and optimized for targeting applications is substantial and may facilitate the introduction of novel therapeutic and diagnostic modalities for treatment of a myriad of diseases including various forms of solid tumors and viral infections.

One application of nanoparticles is drug delivery. There is a need for new particle formulations that can be used to encapsulate drugs.

SUMMARY

Disclosed herein are micro/nano-particles that can be used for delivery of active agents. The particles have excellent stability and high loading efficiency, and can encapsulate multiple agents. Further, the particles can include targeting agents.

In one aspect, the invention features particles that include: an aqueous core; a first amphiphilic layer surrounding the aqueous core; and a polymeric matrix surrounding the first amphiphilic layer. The particles can further include a second amphiphilic layer surrounding the polymeric matrix. Any or all of the aqueous core, first amphiphilic layer, polymeric matrix, and optional second amphiphilic layer can include one or more active agents.

In some embodiments, a particle has an average diameter between about 40 nm and about 400 μm. In some embodiments, a particle has a surface zeta potential ranging from −80 mV to +50 mV.

Either or both of the first and optional second amphiphilic layer can be a monolayer or a multilayer (e.g., a bilayer). In some embodiments, the first and optional second amphiphilic layers include (independently) naturally derived lipids, surfactants, or synthesized compounds with both hydrophilic and hydrophobic moieties. In an exemplary embodiment, the first amphiphilic layer can include 1,2-dimyristoleoyl-sn-glycero-3-ethylphosphocholine (EPC14:1). In another exemplary embodiment, the optional second amphiphilic layer can include lecithin. In some embodiments, the first and optional second amphiphilic layers have (independently) a thickness of about 1 nm to about 50 nm.

In some embodiments, the polymeric matrix includes one or more polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. In some embodiments, the polymeric matrix includes a polyalkylene glycol (e.g., polyethylene glycol (PEG)). In some embodiments, the polymeric matrix includes a polyester (e.g., poly(lactide-co-glycolide) (PLGA), polylactic acid, or polycaprolactone). In some embodiments, the polymeric matrix includes copolymer of two or more polymers, such as a copolymer of a polyalkylene glycol (e.g., PEG) and a polyester (e.g., PLGA). In some embodiments, the polymeric matrix includes a lipid-terminated polyalkylene glycol and a polyester. In some embodiments, the polymeric matrix includes lipid-terminated polyethylene glycol (PEG) and poly(lactide-co-glycolide) (PLGA). The lipid-terminated compound can include a lipid having the structure shown in Formula I:

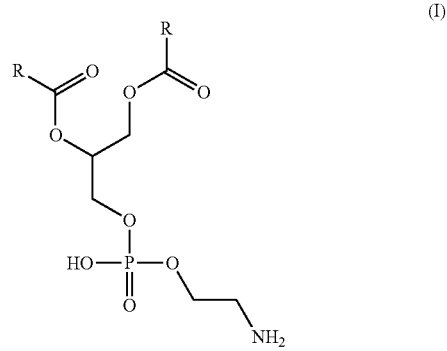

or a salt thereof, wherein each R is, independently, C1-30 alkyl. For example, the lipid can be 1,2 distearoyl-sn-glycero-3-phosphoethanolamine (DSPE) or a salt thereof. In some embodiments, the polymeric matrix includes a biodegradable polymer. In some embodiments, all of the polymers that make up the polymeric matrix are biodegradable.

In some embodiments, the particle includes a targeting agent. The target can be associated with a surface of the particle, e.g., covalently bound to the surface of the particle. In some embodiments, the particle includes a second amphiphilic layer and the targeting agent is conjugated to the hydrophilic region of a molecule of the second amphiphilic layer. In exemplary embodiments, the targeting agent includes a nucleic acid aptamer, polypeptide, protein ligand, small molecule, growth factor, hormone, cytokine, interleukin, antibody, antibody fragment, integrin, fibronectin receptor, carbohydrate, p-glycoprotein receptor, peptide (e.g., including 50 or fewer, 40 or fewer, 30 or fewer, 25 or fewer, 20 or fewer, 16 or fewer, 12 or fewer, 10 or fewer, 9 or fewer, 8 or fewer, or 7 or fewer amino acids), peptidomimetic, hydrocarbon, small modular immunopharmaceutical, or cell binding sequence. In other exemplary embodiments, the targeting agent includes an affibody, nanobody, adnectin, domain antibody, or an avimer, or any combination thereof. Specific examples of targeting agents include those that bind to the Prostate Specific Membrane Antigen (PSMA), e.g., nucleic acids (e.g., A10 RNA aptamer), small molecules, peptides, and antibodies that bind to PSMA. A peptide targeting agent can include, without limitation, one or more of the sequences AKERC (SEQ ID NO:1), CREKA (SEQ ID NO:2), ARYLQKLN (SEQ ID NO:3), KIWKLPQ (SEQ ID NO:29), KVWSLPQ (SEQ ID NO:30), KLWVLPK (SEQ ID NO:31), KIFVWPY (SEQ ID NO:32), and AXYLZZLN (SEQ ID NO:4), wherein X and Z are variable amino acids. In some embodiments, X and Z can be any naturally occurring amino acid, and at least one of Z is occupied by a basic amino acid, preferably lysine or arginine or a chemically modified variant thereof. See U.S. Patent Applications No. 2009/0074828 and 2005/0048063; Dinkla et al., 2007, J. Biol. Chem., 2892:18686-93; and Chan et al., 2010, Proc. Natl. Acad. Sci. USA, 107:2213-18, all of which are incorporated herein by reference in their entirety. In some embodiments, the polymer matrix is covalently bound to the targeting moiety via a maleimide functional group at the free terminus of PEG.

In some embodiments, the particle further includes an antigen. The antigen can be associated with a surface of the particle, e.g., covalently bound to the surface of the particle. In some embodiments, the antigen is conjugated to a hydrophilic region of a molecule of the second amphiphilic layer. Exemplary antigens include proteins, polypeptides, sugars, and small molecules.

In some embodiments, the particle further includes one or more active agents, e.g., one or more therapeutic, immunomodulatory, or diagnostic agents. Exemplary active agents include biomolecules, bioactive agents, small molecules, drugs, prodrugs, proteins, polypeptides, immunogens, haptens, polynucleotides, and adjuvants. Any or all of the aqueous core, first amphiphilic layer, polymeric matrix, and optional second amphiphilic layer can include one or more active agents.

The aqueous core of the particle can include an active agent. Exemplary active agents that can be associated with the aqueous core of the particle include biomolecules, bioactive agents, small molecules, drugs, prodrugs, proteins, polypeptides, immunogens, haptens, polynucleotides, and adjuvants. In some embodiments, the active agent associated with the aqueous core can be a polynucleotide, e.g., an expression vector, siRNA, shRNA, microRNA, ribozyme, or antisense polynucleotide. In some embodiments, the polynucleotide includes an immunostimulatory sequence. The active agent associated with the aqueous core can also be a chemotherapeutic drug or prodrug. Exemplary chemotherapeutic drugs and prodrugs include cisplatin, carboplatin, mitaplatin, oxaliplatin, and irinotecan, and derivatives or prodrugs of any thereof. In some embodiments, the active agent associated with the aqueous core is an imaging agent, e.g., a quantum dot, contrast agent, iron oxide nanoparticle, and/or fluorescent moiety. In some embodiments, the active agent associated with the aqueous core is an immunostimulatory agent, e.g., a toll receptor (TLR) ligand ss/dsRNA, polyI:C polynucleotide, or CpG polynucleotide. In some embodiments, the active agent associated with the aqueous core is selected from irinotecan, dexamethasone phosphate, nicardipine hydrochloride, methylsalicylic acid, nitroglycerine, hydrophilic serotonin 5-HT3 receptor antagonists (e.g., ondansetron, granisetron), aminotetralins (e.g., S(−)-2-(N-propyl-N-2-thienylethylamine)-5-hydroxytetralin), and anthracyclines. In some embodiments, the active agent associated with the aqueous core is an inorganic or organometallic compound, e.g., a platinum compound (e.g., carboplatin, mitaplatin, oxaliplatin, or pyriplatin), a ruthenium compound (e.g., trans-[RuCl$_2$(DMSO)$_4$], trans-[RuCl$_2$(imidazole)$_2$]$^-$, trans-[RuCl$_4$(indazole)$_2$]$^-$, etc.), a cobalt compound, a copper compound, or an iron compound. In some embodiments, the active agent associated with the aqueous core is selected from VEGF, fibroblast growth factors, monocyte chemoattractant protein 1 (MCP-1), transforming growth factor alpha (TGF-alpha), transforming growth factor beta (TGF-beta), DEL-I, insulin like growth factors (IGF), placental growth factor (PLGF), hepatocyte growth factor (HGF), prostaglandin E1 (PG-E1), prostaglandin E2 (PG-E2), tumor necrosis factor alpha (TNF-alpha), granulocyte stimulating growth factor (G-CSF), granulocyte macrophage colony-stimulating growth factor (GM-CSF), angiogenin, follistatin, proliferin, PR39, PRI1, nicotine, hydroxy-methylglutaryl coenzyme A (HMG CoA) reductase inhibitors, statins, niacin, bile acid resins, fibrates, antioxidants, extracellular matrix synthesis promoters, inhibitors of plaque inflammation and extracellular degradation, and estradiol. Additional active agents that can be associated with the aqueous core are described herein. Preferably, an active agent associated with the aqueous core is hydrophilic or amphiphilic.

The polymeric matrix of the particle can include an active agent. Exemplary active agents that can be associated with the polymeric matrix include biomolecules, bioactive agents, small molecules, drugs, prodrugs, immunogens, haptens, and adjuvants. In some embodiments, the active agent associated with the polymeric matrix is a chemotherapeutic drug or prodrug, e.g., paclitaxel, docetaxel, gefitinib, tubacin, or combretastatin, or a derivative or prodrug of any thereof. In some embodiments, the active agent associated with the polymeric matrix is an imaging agent. In some embodiments, the active agent associated with the polymeric matrix is an immunostimulatory agent, e.g., R848 or lipopolysaccharide. Additional active agents that can be associated with the polymeric matrix are described herein. Preferably, an active agent associated with the polymeric matrix is hydrophobic or amphiphilic.

In a further aspect, the invention features a composition that includes a plurality of particles as described above. In some embodiments, the average characteristic dimension of the plurality of particles is 100 µm or less, e.g., 50 µm or less, 20 µm or less, 10 µm or less, 5 µm or less, 1 µm or less, 500 nm or less, 250 nm or less, or 100 nm or less. In some embodiments, the plurality of particles has a polydispersity index of 0.5 or less, e.g., 0.4 or less, 0.3 or less, 0.2 or less, or 0.1 or less. In some embodiments, the composition can be administered to a subject or used in treatment or diagnosis of a subject. The composition can be administered or formulated for administration intravenously, intra-arterially, orally, transdermally, transmucosally, intraperitoneally, intracranially, intraocularly, epidurally, intrathecally, topically, by enema, by injection, by pulmonary route or by infusion.

In another aspect, the invention features methods of preparing a particle that has an aqueous core, a first amphiphilic layer surrounding the aqueous core, and a polymeric matrix surrounding the first amphiphilic layer. The methods can include the steps of: combining a polymeric material and a first amphiphilic compound in a water immiscible organic solvent to form a water immiscible organic solution; adding an aqueous solution optionally containing a first water miscible solvent to the water immiscible organic solution to form a combination; emulsifying the combination to form a first emulsion solution; and evaporating the water immiscible organic solvent and any water miscible solvent to prepare a particle that has an aqueous core, a first amphiphilic layer surrounding the aqueous core, and a polymeric matrix surrounding the first amphiphilic layer. In some embodiments, the methods further include adding a second aqueous solution containing a stabilizer (e.g., PVA) to the first emulsion solution to form a second combination and emulsifying the second combination to form a second emulsion solution, prior to the step of evaporating the water immiscible organic solvent and any water miscible solvent.

In a further aspect, the invention features methods of preparing a particle that has an aqueous core, a first amphiphilic layer surrounding the aqueous core, a polymeric matrix surrounding the first amphiphilic layer, and a second amphiphilic layer surrounding the polymeric matrix. The methods can include the steps of: combining a polymeric material and a first amphiphilic compound in a water immiscible organic solvent to form a water immiscible organic solution; adding a first aqueous solution optionally containing a first water miscible solvent to the water immiscible organic solution to form a first combination; emulsifying the first combination to form a first emulsion solution; adding a second aqueous solution containing a second amphiphilic compound and optionally containing a second water miscible solvent to the first emulsion solution to form a second combination; emulsifying the second combination to form a second emulsion solution; and evaporating the water immiscible organic solvent and any water miscible solvent to prepare a particle that has an aqueous core, a first amphiphilic layer surrounding the aqueous core, a polymeric matrix surrounding the first amphiphilic layer, and a second amphiphilic layer surrounding the polymeric matrix.

In any of the above methods, the polymeric material used can be, without limitation, a biodegradable polymeric material, e.g., polylactic acid, polyglycolic acid, polycaprolactone, or a copolymer of any thereof. In any of the above methods, the first amphiphilic compound can be, without limitation, a naturally derived lipid, surfactant, or a synthesized compound with both hydrophilic and hydrophobic moieties. In any of the above methods, the water immiscible organic solvent can include, without limitation, one or more of chloroform, dichloromethane, and acyl acetate. In any of the above methods, the first aqueous solution can optionally include an active agent, e.g., an active agent described herein. In any of the above methods, the first water miscible solvent can include, without limitation, one or more of acetone, ethanol, methanol, and isopropyl alcohol. In any of the above methods, the step of emulsifying the combination to form a first emulsion solution can include, e.g., sonication or homogenization. In any of the above methods, the water immiscible organic solution can optionally include a second active agent, e.g., an active agent described herein. In any of the above methods, the second amphiphilic compound can optionally include a targeting agent conjugated to the hydrophilic region of the second amphiphilic compound. In any of the above methods, the second amphiphilic compound can include an antigen conjugated to its hydrophilic region.

In another aspect, the invention features methods of treating a disorder by administering to a subject a particle (or a composition that includes a plurality of particles) as described herein that includes one or more active agents, wherein the one or more active agents are effective to treat the disorder. The invention also features the use of a particle (or a composition that includes a plurality of particles) as described herein that includes one or more active agents in the treatment of a disorder, wherein the one or more active agents are effective to treat the disorder.

In a further aspect, the invention features methods of inducing an immune response by administering to a cell or a subject a particle (or a composition that includes a plurality of particles) as described herein that includes one or more active agents, wherein the one or more active agents include an immunomodulatory agent (e.g., an antigen) and/or an immunostimulatory agent (e.g., an adjuvant). The invention also features the use of a particle (or a composition that includes a plurality of particles) as described herein that includes one or more active agents in the induction of immune response in a cell or subject, wherein the one or more active agents include an immunomodulatory agent (e.g., an antigen) and/or an immunostimulatory agent (e.g., an adjuvant).

In another aspect, the invention features methods of decreasing expression of a polynucleotide by administering to a cell or a subject a particle (or a composition that includes a plurality of particles) as described herein that includes one or more active agents, wherein the one or more active agents include an inhibitory nucleic acid (e.g., an siRNA, shRNA, microRNA, ribozyme, or antisense polynucleotide) specific for the polynucleotide. The invention also features the use of a particle (or a composition that includes a plurality of particles) as described herein that includes one or more active agents in a method of decreasing expression of a polynucleotide in a cell or subject, wherein the one or more active agents include an inhibitory nucleic acid (e.g., an siRNA, shRNA, microRNA, ribozyme, or antisense polynucleotide) specific for the polynucleotide.

The term "nanoparticle," as used herein, can refer to both nano-scale and micro-scale particles and, except where otherwise noted, is generally synonymous with the term "particle."

The particles described herein provide several advantages. An inner aqueous core surround by amphiphilic compounds can efficiently encapsulate hydrophilic active agents including nucleic acids, proteins, peptides, and small molecules. Meanwhile, a polymeric layer can encapsulate hydrophobic active agents. When the polymeric layer is covered with a thin film of one or more amphiphilic compounds, the new particles have merits of both polymer- and lipid-based nanoparticles, while excluding some of their limitations. The amphiphilic compounds can form a tightly assembled layer around the polymeric layer. This outer amphiphilic layer can prevent the carried agents from diffusing freely out of the particles, thereby enhancing the encapsulation yield and controlling, e.g., slowing, drug release. Moreover, the outer amphiphilic layer can reduce water penetration rate into the nanoparticle, which can slow the degradation rate of the biodegradable polymers, thereby increasing particle stability and lifetime. In addition, by conjugating targeting ligands to the amphiphilic component prior to incorporating them into the nanoparticle, the composition of the nanoparticle and its surface properties can be more accurately quantified.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A to 1D are a series of schematic diagrams of four exemplary particle structures as described herein.

DETAILED DESCRIPTION

Figure 2A:
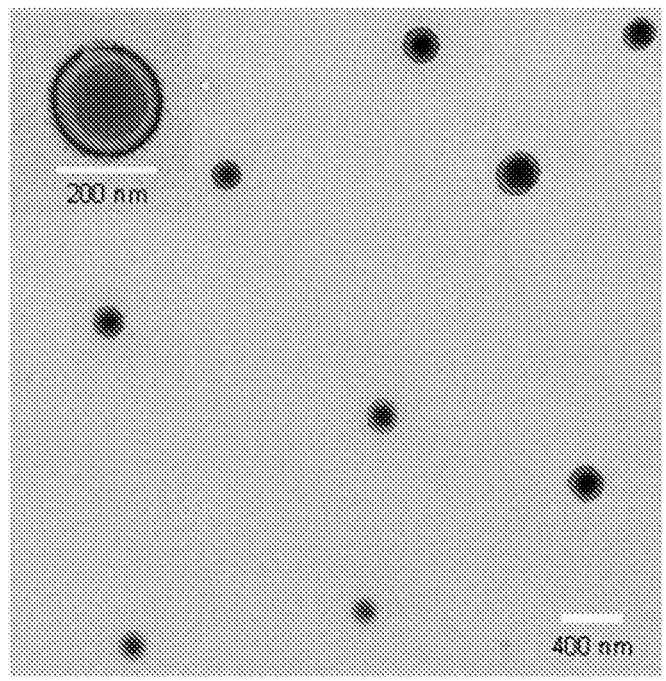
FIGS. 2A and B are transmission electron microscopy (2A) and laser scanning confocal fluorescence (2B) micrographs of lipid-polymer-lipid particles. The scale bar in FIG. 2B represents 10 μm.

The present invention provides, inter alia, a platform technology that enables the formulation of micro/nanoparticles with improved properties as compared to both polymer-based nanocarriers and lipid-based liposomes.

In one embodiment, the invention features a particle that includes an aqueous core; an amphiphilic layer surrounding the aqueous core; and a polymeric matrix surrounding the first amphiphilic layer. The inner aqueous core surround by amphiphilic compounds can efficiently encapsulate hydrophilic agents, e.g., nucleic acids, proteins, peptides, or small molecules. The polymeric coating layer can be used, e.g., to encapsulate hydrophobic drugs. In some embodiments, the polymeric layer is further covered with a thin film of amphiphilic compounds and/or conjugated targeting molecules). The particles described herein have advantages of both polymer- and lipid-based nanoparticles, while excluding many of their limitations.

FIG. 1A depicts an exemplary particle formulation. An aqueous core optionally containing a nucleic acid (e.g., siRNA) is surrounded by an inner lipid (e.g., EPC14:1) layer. The hydrophobic portions of the inner lipids interact with a polymeric shell (e.g., PLGA), which optionally encapsulates a drug (e.g., docetaxel). The polymeric shell, in turn, is surrounded by an outer lipid layer that includes one or more lipids (e.g., lecithin) and a PEGylated lipid (e.g., DSPE-PEG).

FIG. 1B depicts another exemplary particle formulation. An aqueous core optionally containing a nucleic acid (e.g., siRNA) is surrounded by an inner lipid (e.g., EPC14:1) layer. The hydrophobic portions of the inner lipids interact with a polymeric shell (e.g., PLGA), which optionally encapsulates a drug (e.g., docetaxel). The polymeric shell, in turn, is surrounded by an outer lipid layer that includes one or more PEGylated lipids (e.g., DSPE-PEG).

FIG. 1C depicts an additional exemplary particle formulation. An aqueous core optionally containing a nucleic acid (e.g., siRNA) is surrounded by an inner lipid (e.g., EPC14:1) layer. The hydrophobic portions of the inner lipids interact with a polymeric shell (e.g., PLGA), which optionally encapsulates a drug (e.g., docetaxel). The polymeric shell, in turn, is surrounded by an outer lipid layer that includes one or more lipids (e.g., lecithin).

FIG. 1D depicts another exemplary particle formulation. An aqueous core optionally containing a nucleic acid (e.g., siRNA) is surrounded by an inner lipid (e.g., EPC14:1) layer. The hydrophobic portions of the inner lipids interact with a polymeric shell (e.g., PLGA), which optionally encapsulates a drug (e.g., docetaxel). The polymeric shell, in turn, is surrounded by an outer surfactant (e.g., polyvinyl alcohol) layer.

The particles, e.g., lipid-polymer hybrid micro- and nanoparticles, can be produced such that they are biodegradable, such that they include materials already approved by government regulatory agencies, and/or such that they result in a submicron size (e.g., 10 nm-1000 nm or other ranges, e.g., 25 nm-250 nm, e.g., 15 nm-50 nm, 10 nm-500 nm), or a micron-scale size. Nano-scale particles are considered herein to be up to 1000 nm at their largest cross-sectional dimension. Micron-scale particles are over 1.0 micron at their largest cross-sectional dimension (e.g., 1.0 micron up to 100 microns, or larger, e.g., 1.0 to 2.0 microns, 1.0 to 10.0 microns, 5 to 25 microns, and 25 to 50 microns), and can also be made according to the methods described herein.

In some cases, the particle has a characteristic dimension of less than 400 micrometers, where the characteristic dimension is the largest cross-sectional dimension of a particle. For example, the particle can have a characteristic dimension of less than about 300 µm, less than about 200 µm, less than about 100 µm, less than about 50 µm, less than about 20 µm, less than about 10 µm, less than about 5 µm, less than about 2 µm, less than about 1 µm, less than about 500 nm, less than about 400 nm, less than about 250 nm, less than about 200 nm, less than about 150 nm, less than about 100 nm, less than about 50 nm, or less than about 40 nm in some cases.

In some cases, a population of particles can be present. Various embodiments of the present invention are directed to such populations of particles. For instance, in some embodiments, the population of particles can have an average characteristic dimension of less than about 400 µm, less than about 300 µm, less than about 200 µm, less than about 100 µm, less than about 50 µm, less than about 20 µm, less than about 10 µm, less than about 5 µm, less than about 2 µm, less than about 1 µm, less than about 500 nm, less than about 400 nm, less than about 250 nm, less than about 200 nm, less than about 150 nm, less than about 100 nm, less than about 50 nm, or less than about 40 nm in some cases. In some embodiments, the particles can each be substantially the same shape and/or size ("monodisperse"). For example, the particles can have a distribution of characteristic dimensions such that no more than about 5% or about 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater than the average characteristic dimension of the particles. In some cases, no more than about 5% of the particles have a characteristic dimension greater than about 5%, about 3%, about 1%, about 0.3%, about 0.1%, about 0.03%, or about 0.01% greater than the average characteristic dimension of the particles.

In some embodiments, the diameter of no more than 25% of the produced particles varies from the mean particle diameter by more than 150%, 100%, 75%, 50%, 25%, 20%, 10%, or 5% of the mean particle diameter. It is often desirable to produce a population of particles that is relatively uniform in terms of size, shape, and/or composition so that each particle has similar properties. For example, at least 80%, at least 90%, or at least 95% of the particles produced using the methods described herein can have a diameter or greatest dimension that falls within 5%, 10%, or 20% of the average diameter or greatest dimension. In some embodiments, a population of particles can be heterogeneous with respect to size, shape, and/or composition. See, e.g., WO 2007/150030, which is incorporated herein by reference in its entirety.

In some embodiments, the polydispersity index of a population of particles is 0.6 or less, e.g., 0.5 or less, 0.4 or less, 0.3 or less, 0.2 or less, 0.1 or less, or 0.05 or less.

In many embodiments, the particles are formulated for controlled release. Controlled release occurs when a natural or synthetic polymer and/or amphiphilic compound are combined with one or more active agent in such a way that the active agent(s) are retained within the polymer system for subsequent release in a predetermined manner. Lipid-polymer hybrid particles can release the encapsulated active agents through surface or bulk erosion, diffusion, and/or swelling followed by diffusion, in a time or condition dependent manner. The release of the active agent can be constant over a long or short period, it can be cyclic over a long or short period, or it can be triggered by the environment or other external events (see, e.g., Langer and Tirrell, 2004, Nature, 428:487-492). In general, controlled-release polymer systems can provide drug levels in a specific range over a longer period of time than other drug delivery methods, thus increasing the efficacy of the drug and maximizing patient compliance.

Without wishing to be bound by theory, the particle parameters, e.g., amphiphilic compound composition and configuration, size, charge, etc., can alter the delivery (e.g., loss of payload, drug efflux, aggregations, delivery to desired location, etc.) of the active agents from the particles. In some cases, larger particles tend to lose their payload more quickly than smaller particles and/or a drug efflux may be more rapid from smaller particles than larger particles. Smaller particles, in some cases, can be more likely to aggregate than larger particles. The size of the particle may affect the distribution of the particles throughout the body. For example, larger particles injected into a bloodstream may be more likely to be lodged in small vessels than smaller particles. In some instances, larger particles may be less likely to cross biological barriers (e.g., capillary walls) than smaller particles. The size of the particles used in a delivery composition can be selected based on the application, and will be readily known to those of ordinary skill in the art. For example, particles of smaller size (e.g., <200 nm) can be selected if systematic delivery of the particles throughout a patient's bloodstream is desired. As another example, particles of larger size (e.g., >200 nm) can be selected if sequestering of the particles by a patient's reticuloendothelial system upon injection is desired (e.g., sequestering of the particles in the liver, spleen, etc.). The desired length of time of delivery can also be considered when selecting particle size. For example, smaller particles tend to circulate in the blood stream for longer periods of time than larger particles.

In some embodiments, the particles are designed to substantially accumulate at the site of a specific target, e.g., a tumor. In some embodiments, this may be due, at least in part, to the presence of a targeting moiety associated with the particle, as described herein. In some embodiments, this may be due, at least in part, to an enhanced permeability and retention (EPR) effect, which allows for particles to accumulate specifically at a tumor site. The EPR effect will be known to those of ordinary skill in the art and refers to the property by which certain sizes of material (e.g., particles) tend to accumulate in tumor tissue much more than they do in normal tissues.

When amphiphilic compounds are present surrounding the polymeric layer, this layer can effectively prevent the carried agents from freely diffusing out of the nanoparticle, thereby enhancing the encapsulation yield and slowing drug release. Moreover, an outer amphiphilic layer can reduce water penetration rate into the nanoparticle, which slows hydrolysis rate of the biodegradable polymers, thereby increasing particle stability and lifetime.

The particles described herein are useful in drug delivery for therapeutic applications. In an alternative embodiment, these particles are useful for molecular imaging, for diagnostic applications, or for a combination thereof ("theranostics").

Amphiphilic Compounds

As used herein, the term "amphiphilic" refers to a molecule having both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the invention, the amphiphilic compound can be, but is not limited to, one or a plurality of the following: naturally derived lipids, surfactants, or synthesized compounds with both hydrophilic and hydrophobic moieties.

Specific examples of amphiphilic compounds that may be included in an amphiphilic layer include, but are not limited to, phospholipids, sphingolipids (e.g., sphingomyelin), diphosphatidylglycerol lipids (e.g., cardiolipin). Exemplary classes of phospholipids include phosphatidic acids, phosphatidylethanolamines, phosphatidylcholines, phosphatidylglycerols, phosphatidylserines, phosphoinositides, phosphatidylinositols, sphingomyelin, lysophosphatidyl derivatives, cardiolipin, and β-acyl-y-alkyl phospholipids. In some embodiments, the amphiphilic compound is a synthetic phospholipid derivative, such as a phosphocholine, phosphoglycerol, phosphatidic acid, phosphoethanolamine, phosphoserine, or PEG phospholipid. Phospholipids and derivatives that may be used can include either saturated or unsaturated lipids, or both. In some embodiments, synthetic phospholipids with asymmetric acyl chains (e.g., with one acyl chain of 6 carbons and another acyl chain of 12 carbons) can also be used. Specific phospholipids that can be used include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); phosphatidylethanolamines such as dioleoylphosphatidylethanolamine or 1-hexadecyl-2-palmitoylglycerophosphoethanolamine; phosphocholines such as 1,2-dimyristoleoyl-sn-glycero-3-ethylphosphocholine (EPC14:1); and phosphoethanolamines such as 1,2-distearoyl-sn-glycero-3-phosphoethanolamine (DSPE).

In some embodiments, the amphiphilic compound can have a molecular weight of 200 to 1000, e.g., 700 to 900. In some embodiments, the particles described herein comprise approximately 5% to 20% lipid (by weight).

In particular embodiments, an amphiphilic compound that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices.

In certain embodiments, an amphiphilic component of the particles described herein can include a surfactant, e.g., polyvinyl alcohol (PVA), dioctyl sodium sulfosuccinate, methyl cellulose, polysorbates, cetyltrimethylammonium bromide (CTAB), dodecylamine (DDA), 1,2-di-O-octadecenyl-3-trimethylammonium propane (DOTMA), or 1,2-Dioleoyl-3-trimethylammonium-propane (DOTAP). Various surfactants useful in the disclosed compositions are described in Martin Malmsten, *Surfactants and Polymers in Drug Delivery*, Informa Healthcare, 2002.

In certain embodiments, the amphiphilic compound is a cationic lipid. Exemplary cationic lipids include 1,2-Dilinoleyloxy-N,N-dimethylaminopropane (DLinDMA), 1,2-Dilinolenyloxy-N,N-dimethylaminopropane (DLenDMA), N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), distearyldimethylammonium (DS-DMA), N-(1-(2,3-dioleyloxy)propyl)-N,N,N-trimethylammonium chloride (DOTMA), N,N-dimethyl-2,3-dioleyloxypropylamine (DODMA), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propan-amin-iumtrifluoroacetate (DOSPA), dioctadecylamidoglycyl spermine (DOGS), 3-dimethylamino-2-(cholest-5-en-3-beta-oxybutan-4-oxy)-1-(cis,cis-9, 12-oc-tadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), and 1,2-Dilinoleoylcarbamyl-3-dimethyl-aminopropane (DLinCDAP). Additional exemplary cationic lipids are disclosed in WO 2009/088891; WO 2009/086558; WO 2010/042877; and Semple et al., 2010, Nature Biotechnol., 28:172-176, all of which are incorporated by reference herein.

In certain embodiments, the amphiphilic compound is a lipid-like compound, e.g., an amino-alkyl-acrylate, an amino-alkyl-acrylamide, or an amino alcohol. Such amine-containing lipid-like compounds (amino-alkyl-acrylates, amino-alkyl-acrylamides, and amino alcohols) are also known as "lipidoids". Exemplary lipidoids include those disclosed in WO 2010/062322; WO 2010/053572; US 2009/0023673; Akinc et al., 2008, Nature Biotechnol., 26:561-569; Akinc et al., 2009, Mol. Ther., 17:872-879; and Love et al., 2010, Proc. Natl. Acad. Sci. USA, 107:1864-69, all of which are incorporated by reference herein.

An amphiphilic component of the particles described herein can include a combination of amphiphilic compounds (e.g., a mixture of two, three, four or more amphiphilic compounds).

In certain embodiments of the invention, an amphiphilic layer of the particle is a monolayer, meaning the layer is not a phospholipid bilayer, but exists as a single continuous or discontinuous layer around, or within, the particle. A monolayer has the advantage of allowing the particles to be smaller in size, which makes them easier to prepare. The amphiphilic layer can be "associated with" the particle of the invention, meaning it is positioned in some proximity to the polymeric matrix, such as surrounding the outside of the polymeric matrix (e.g., PLGA), or dispersed within the polymers that make up the particle.

In some embodiments, the particles disclosed herein include a stealth polymer (e.g., an inert, non-degradable polymer such as PEG), wherein the stealth polymer is covalently bound to an amphiphilic compound. See, e.g., Yokoyama et al., Cancer Research 51:3229, 1991; Gref et al., Science 263:1600, 1994; Gref et al., Advanced Drug Delivery Reviews 16:215, 1995; Klibanov et al., FEBS Lett. 268:235, 1990; VertutDoi et al., Biochimica BiophysicaActa—Biomembranes 1278:19, 1996; and Gref et al., Colloids Surfaces B—Biointerfaces 18:301, 2000. In some embodiments, the particles disclosed herein include a targeting agent covalently bound to a stealth polymer, wherein the stealth polymer is covalently bound to an amphiphilic compound. In further embodiments, the particles disclosed herein include a targeting compound covalently bound to an amphiphilic compound, wherein the targeting compound is further covalently bound to stealth polymer. In some embodiments, the amphiphilic layer comprises a mixture of amphiphilic compounds, wherein a portion of the amphiphilic compounds in the mixture are covalently bound to one or more of a targeting agent and/or a stealth polymer.

In one embodiment, upon being administered to a subject, particles having an outer amphiphilic layer can degrade, such that the polymer core is eventually "unshielded." Such a process, particularly when occurring after penetration into target tissue, can lead to more efficient delivery of the therapeutic agent, thereby affording an enhanced therapeutic effect.

Polymers

A wide variety of polymers and methods for forming particles therefrom are known in the art. In some embodiments, the particles disclosed herein include a matrix made up of one or more polymers. Any polymer may be used in accordance with the present invention. Polymers may be natural or unnatural (synthetic) polymers. Polymers may be homopolymers or copolymers comprising two or more monomers. In terms of sequence, copolymers may be random, block, or comprise a combination of random and block sequences. Polymers used in accordance with the present invention can be, e.g., organic polymers.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer. In some cases, additional moieties can also be present in the polymer, for example targeting moieties such as those described herein.

If more than one type of repeat unit is present within the polymer, then the polymer is said to be a "copolymer." It is to be understood that in any embodiment employing a polymer, the polymer being employed can be a copolymer in some cases. The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In some embodiments, a polymer is hydrophobic. In some embodiments, a polymer is amphiphilic, i.e., having a hydrophilic portion and a hydrophobic portion, or a relatively hydrophilic portion and a relatively hydrophobic portion. A hydrophilic polymer is one that generally attracts water and a hydrophobic polymer is one that generally repels water. A hydrophilic or a hydrophobic polymer can be identified, for example, by preparing a sample of the polymer and measuring its contact angle with water (typically, a hydrophilic polymer will have a contact angle of less than about 50°, while a hydrophobic polymer will have a contact angle of greater than about 50°). In some cases, the hydrophilicity of two or more polymers can be measured relative to each other, i.e., a first polymer can be more or less hydrophilic than a second polymer. For instance, the first polymer can have a smaller contact angle than the second polymer. In embodiments containing more than two polymers, the polymers can be ranked in order by comparing their solubility parameters.

In one set of embodiments, the polymer base component (e.g., polymer) can be biocompatible, i.e., a polymer that does not typically induce an adverse response when inserted or injected into a living subject, for example, without significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the lack of acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject.

One simple test to determine biocompatibility is to expose a polymer to cells in vitro; biocompatible polymers are polymers that typically do not result in significant cell death at moderate concentrations, e.g., at concentrations of about 50 micrograms/$10^6$ cells. For instance, a biocompatible polymer may cause less than about 20% cell death when exposed to cells such as fibroblasts or epithelial cells, even if phagocytosed or otherwise taken up by such cells. Non-limiting examples of biocompatible polymers that can be useful in various embodiments of the present invention include polydioxanones (PDO), polyhydroxyalkanoates, polyhydroxybutyrates, poly(glycerol sebacate)s, polyglycolides, polylactides, polycaprolactones, polyanhydrides or copolymers or derivatives including these and/or other polymers.

In certain embodiments, the biocompatible polymer is biodegradable, i.e., the polymer is able to degrade, chemically and/or biologically, within a physiological environment, such as within the body. For instance, the polymer can be one that hydrolyzes spontaneously upon exposure to water (e.g., within a subject), the polymer can degrade upon exposure to heat (e.g., at temperatures of about 37° C.). Degradation of a polymer can occur at varying rates, depending on the polymer or copolymer used. For example, the half-life of the polymer (the time at which 50% of the polymer is degraded into monomers and/or other nonpolymeric moieties) can be on the order of days, weeks, months, or years, depending on the polymer. The polymers can be biologically degraded, e.g., by enzymatic activity or cellular machinery, in some cases, for example, through exposure to a lysozyme (e.g., having relatively low pH). In some cases, the polymers can be broken down into monomers and/or other nonpolymeric moieties that cells can either reuse or dispose of without significant toxic effect on the cells (for example, polylactide can be hydrolyzed to form lactic acid, polyglycolide can be hydrolyzed to form glycolic acid, etc.). Examples of biodegradable polymers include, but are not limited to, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids;

PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene inline), PEGylated poly(ethylene imine), poly(L-lactide-co-L-lysine), poly(serine ester), poly(4-hydroxy-L-proline ester), poly[a-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

Various polymers useful in the disclosed compositions are described in Martin Malmsten, *Surfactants and Polymers in Drug Delivery*, Informa Healthcare, 2002.

In particular embodiments, by optimizing the ratio of lactic acid to glycolic acid monomers in the polymer of the nanoparticle (e.g., a PLGA block copolymer or PLGA-PEG block copolymer), parameters such as water uptake, therapeutic agent release (e.g., "controlled release") and polymer degradation kinetics can be optimized. Typically, the higher the content of glycolide units, the lower the time required for degradation.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid), polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In another set of embodiments, a polymer of the present invention can be able to control immunogenicity, for example a poly(alkylene glycol) (also known as poly(alkylene oxide)), such as polypropylene glycol), or poly(ethylene oxide), also known as poly(ethylene glycol) ("PEG"), having the formula —$(CH_2—CH_2—O)_n$—, where n is any positive integer. In some embodiments, branched PEGs can be used (see, e.g., Veronese et al., 2008, BioDrugs, 22:315-329; Hamidi et al., 2006, Drug Deliv., 13:399-409). The poly(ethylene glycol) units can be present within the polymeric base component in any suitable form. For instance, the polymeric base component can be a block copolymer where one of the blocks is poly(ethylene glycol).

A polymer comprising poly(ethylene glycol) repeat units is also referred to as a "PEGylated" polymer. Such polymers can control inflammation and/or immunogenicity (i.e., the ability to provoke an immune response), due to the presence of the poly(ethylene glycol) groups. PEGylation can also be used, in some cases, to decrease charge interaction between a polymer and a biological moiety, e.g., by creating a hydrophilic layer on the surface of the polymer, which can shield the polymer from interacting with the biological moiety. For example, PEGylation can be used to create particles which comprise an interior which is more hydrophobic than the exterior of the particles. In some cases, the addition of poly(ethylene glycol) repeat units can increase plasma half-life of the polymeric conjugate, for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, for example, by ring opening polymerization techniques (ROMP), or the like. In addition, certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds).

In a particular embodiment, the molecular weight of the polymers of the nanoparticles of the invention are optimized for effective treatment of diseases, e.g., cancer. For example, the molecular weight of the polymer influences nanoparticle degradation rate (particularly when the molecular weight of a biodegradable polymer is adjusted), solubility, water uptake, and drug release kinetics (e.g. "controlled release").

As a further example, the molecular weight of the polymer can be adjusted such that the nanoparticle biodegrades in the subject being treated within a reasonable period of time (ranging from a few hours to 1-2 weeks, 3-4 weeks, 5-6 weeks, 7-8 weeks, etc.). In particular embodiments of a nanoparticle comprising a copolymer of PEG and PLGA, the PEG has a molecular weight of 1,000-20,000, e.g., 5,000-20,000, e.g., 10,000-20,000, and the PLGA has a molecular weight of 5,000-100,000, e.g., 20,000-70,000, e.g., 20,000-50,000.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al, 2001, J. Am. Chem. Soc, 123:9480; Lim et al., 2001, J. Am. Chem. Soc., 123:2460; Langer, 2000, Ace. Chem. Res., 33:94; Langer, 1999, J. Control. Release, 62:7; and Uhrich et al, 1999, Chem. Rev., 99:3181). More generally, a variety of methods for synthesizing suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al, 1997, Nature, 390:386; and in U.S. Pat. Nos. 6,506,577, 6,632,922, 6,686,446, and 6,818,732.

Targeting Agents

In certain embodiments the particles disclosed herein can be modified to include targeting agents that will direct the particle to a particular cell type, collection of cells, or tissue. Preferably, the targeting agents are associated with the surface of the particles. A variety of suitable targeting agents are known in the art (Cotten et al., Methods Enzym. 217: 618, 1993; Torchilin, Eur. J. Pharm. Sci. 11:881, 2000; Garnett, Adv. Drug Deliv. Rev. 53:171, 2001; Peer et al., Nat. Nanotech. 2:751, 2007). For example, any of a number of different materials that bind to antigens on the surfaces of target cells can be employed. Antibodies to target cell surface antigens will generally exhibit the necessary specificity for the target. In addition to antibodies, suitable immunoreactive fragments can also be employed, such as the Fab, Fab', or F(ab')2 fragments. Many antibody fragments suitable for use in forming the targeting mechanism are already available in the art. Similarly, ligands for any receptors on the surface of the target cells can suitably be employed as targeting agent. These include any small molecule or biomolecule, natural or synthetic, which binds specifically to a cell surface receptor, protein or glycoprotein found at the surface of the desired target cell.

There are other targeting agents, such as nucleic acid ligands, such as aptamers, which are small oligonucleotides that specifically bind to certain target molecules and are potential candidates to target proteins over-expressed in cancer cells, such as prostate cancer cells. A nucleic acid ligand is a nucleic acid that can be used to bind to a specific molecule. For example, pegaptanib is a pegylated anti-VEGF aptamer, a single stranded nucleic acid that binds with high specificity to a particular target. Although the pegaptanib aptamer was originally approved by FDA in 2004 to treat age-related macular degeneration (AMD) disease, it has the potential to treat prostate cancer because it binds specifically to VEGF165, a protein recognized as the key inducer of tumor angiogenesis. Latil et al., Int. J. Cancer, 89, 167-171 (2000) suggests that VEGF expression could be used as a prognostic marker in early-stage tumors. Specific aptamers include, for example, Aptamer O-7 which binds to osteoblasts; A10 RNA aptamer, which binds to prostate cancer cells; aptamer TTA1, which binds to breast cancer cells; and the extended A9 RNA aptamer (Javier et al., Bioconjug. Chem., 2008, 19:1309-12). See also, Wilson et al., U.S. Published Patent Application No. 20090105172. In general, aptamers are stable in a wide range of pH (~4-9), physiological conditions, and solvents. Aptamers are known to be less immunogenic than antibodies and can penetrate a tumor more easily because of size. The shape of aptamer binding sites, which includes grooves and clefts, provide highly specific characteristics and drug-like capabilities. Active targeting, however, requires that the RNA aptamers discriminate cancer cells from normal cells.

Other exemplary targeting agents include peptides, such as CLT1 and CLT2, which bind to fibrin-fibronectin complexes in blood clots. Various peptides are well known in the art for binding to cells in the brain, kidneys, lungs, skin, pancreas, intestine, uterus, adrenal gland, and prostate, including those described in Pasqualini et al., Mol. Psychiatry, 1:421-422 (1996) and Rajotte et al., J. Clin. Invest., 102:430-437 (1998), for example.

In one aspect of the invention, there can be two or more distinct targeting agents bound to the surface of a particle. A primary target can be an immune system cell, such as a leukocyte or T-cell, and a secondary target can be a malignant cancer cell(s) within a tumor, which is the target region. The targeting agent on the surface of the particle binds to the primary target cell with high selectivity, while the second moiety has a general tumor targeting surface domain. Suitable moieties for binding with targets include those described herein. Thus, after delivery of the particles to the target tissue, the particles having tumor targeting moieties can bind with the secondary target (e.g., cancer) cells, once they detach from originally targeted cells. In certain aspects, a particle delivery composition is provided for active agent delivery that is long-circulating, highly selective, and enables the release of multiple drugs with complex release kinetics.

Other targeting agents include agents that specifically bind to biological targets such as a particular immune system cell (e.g., a T cell or B cell), a protein, an enzyme, or other circulating agent associated with a subject. The following are exemplary and non-limiting examples of suitable targeting moieties for use with the multifunctionalized particles described herein. Proteins, such as heat shock protein HSP70 for dendritic cells and folic acid to target cancer cells. Polysaccharides or sugars, such as silylic acid for targeting leucocytes, targeting toxins such as saporin, antibodies, including CD-2, CD-3, CD-28, T-cells, and other suitable antibodies are listed in a Table available on the internet on the World Wide Web at "researchd.com/rdicdabs/cdindex.htm", as revised May 2, 2007, and incorporated herein by reference.

The term "binding," as used herein, refers to the interaction between a corresponding pair of molecules or portions thereof that exhibit mutual affinity or binding capacity, typically due to specific or non specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to binding by molecules, such as polynucleotides, antibodies, and other ligands, that are able to bind to or recognize a binding partner (or a limited number of binding partners) to a substantially higher degree than to other, similar biological entities. In one set of embodiments, the targeting moiety has a specificity (as measured via a disassociation constant) of less than about 1 micromolar, at least about 10 micromolar, or at least about 100 micromolar.

Non-limiting examples of targeting agents include a peptide, a protein, an enzyme, a nucleic acid, a fatty acid, a hormone, an antibody, a carbohydrate, a peptidoglycan, a glycopeptide, or the like. These and other targeting agents are discussed in detail below. In some cases, the biological targeting moiety can be relatively large, for example, for peptides, nucleic acids, or the like. For example, the biological moiety can have a molecular weight of at least about 1,000 Da, at least about 2,500 Da, at least about 3000 Da, at least about 4000 Da, or at least about 5,000 Da, etc. Relatively large targeting agents can be useful, in some cases, for differentiating between cells. For instance, in some cases, smaller targeting agents (e.g., less than about 1000 Da) may not have adequate specificity for certain targeting applications, such as targeting applications. In contrast, larger molecular weight targeting agents can offer a much higher targeting affinity and/or specificity. For example, a targeting agent can offer smaller dissociation constants, e.g., tighter binding. However, in other embodiments, the targeting agent can be relatively small, for example, having a molecular weight of less than about 1,000 Da or less than about 500 Da.

In one embodiment, the targeting agent includes a protein or a peptide. "Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids. A protein can be, for example, a protein drug, an antibody, an antibody fragment, a recombinant antibody, a recombinant protein, an enzyme, or the like. In some cases, one or more of the amino acids of the protein or peptide can be modified in some instances, for example, by the addition of a chemical entity such as a carbohydrate group, a phosphate group, a farnesyl group, an isofarnesyl group, a fatty acid group, a linker for conjugation, functionalization, or other modification, etc.

Other examples of peptides or proteins include, but are not limited to, ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, CD168, lymphocyte function-associated antigen, intercellular adhesion molecule, vascular cell adhesion molecule, Thy-1, antiporters, CA-15-3 antigen, fibronectins, laminin, myelin-associated glycoprotein, GAP, and GAP43. Other examples include affibodies, nanobodies, Avimers, Adnectins, domain antibodies, and small modular immunopharmaceuticals (SMIP™) (Trubion Pharmaceuticals Inc., Seattle, Wash.).

As used herein, an "antibody" refers to a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases.

Non-limiting examples of antibodies and other suitable targeting agents include anti-cluster of differentiation antigen CD-1 through CD-166 and the ligands or counter receptors for these molecules; anti-cytokine antibodies, e.g., anti-IL-1 through anti-IL-18 and the receptors for these molecules; anti-immune receptor antibodies, antibodies against T cell receptors, major histocompatibility complexes I and II, B cell receptors, selectin killer inhibitory receptors, killer activating receptors, OX-40, MadCAM-1, Gly-CAM1, integrins, cadherens, sialoadherens, Fas, CTLA-4, Fc-gamma receptor, Fc-alpha receptors, Fc-epsilon receptors, Fc-mu receptors, and their ligands; anti-metalloproteinase antibodies, e.g., collagenase, MMP-1 through MMP-8, TIMP-1, TIMP-2; anti-cell lysis/proinflammatory molecules, e.g., perforin, complement components, prostanoids, nitrous oxide, thromboxanes; or anti-adhesion molecules, e.g., carcinoembryonic antigens, lamins, or fibronectins.

Other examples of targeting agents include cytokines or cytokine receptors, such as Interleukin-1 (IL-1), IL-2, IL-3, IL-4, IL-5, IL-6, IL-7, IL-8, IL-9, IL-10, IL11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor beta, tumor necrosis factor, lymphotoxin, Fas, granulocyte colony stimulating factor, granulocyte macrophage colony stimulating factor, interferon alpha, interferon beta, interferon gamma.

Still other examples of targeting agents include growth factors and protein hormones, for example, erythropoietin, angiogenin, hepatocyte growth factor, fibroblast growth factor, keratinocyte growth factor, nerve growth factor, tumor growth factor alpha, thrombopoietin, thyroid stimulating factor, thyroid releasing hormone, neurotrophin, epidermal growth factor, VEGF, ciliary neurotrophic factor, LDL, somatomedin, insulin growth factor, or insulin-like growth factor I and II.

Additional examples of targeting agents include chemokines, for example, ENA-78, ELC, GRO-alpha, GRO-beta, GRO-gamma, HRG, LIF, IP-10, MCP-1, MCP-2, MCP-3, MCP-4, MIP-1 alpha, MIP-1 beta, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, alpha-chemokine receptors such as CXCR1, CXCR2, CXCR3, CXCR4, CXCR5, CXCR6, CXCR7, or beta-chemokine receptors such as CCR1, CCR2, CCR3, CCR4, CCR5, CCR6, or CCR7.

In another embodiment, the targeting agent includes a nucleic acid. The term "nucleic acid," or "oligonucleotide," as used herein, refers to a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide can be, for example, ribose sugars (a "ribonucleic acid," or "RNA"), or deoxyribose sugars (a "deoxyribonucleic acid," or "DNA"). In some cases, the polymer can comprise both ribose and deoxyribose sugars. Examples of bases include, but not limited to, the naturally-occurring bases (e.g., adenosine or "A," thymidine or "T," guanosine or "G," cytidine or "C," or uridine or "U"). In some cases, the polymer can also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynyl-cytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide can include DNA, RNA, modified DNA, modified RNA, antisense oligonucleotides, expression plasmid systems, nucleotides, modified nucleotides, nucleosides, modified nucleosides, intact genes, or combinations thereof. Other examples of polynucleotides include interfering RNA, natural or unnatural siRNAs, shRNAs, microRNAs, ribozymes, DNA plasmids, antisense oligonucleotides, randomized oligonucleotides, or ribozymes.

Tumor targeted particles can be delivered into the tumor via the passive or active process. In the former, nanoparticles pass through leaky tumor capillary fenestrations into the tumor interstitium and cells by passive diffusion or convection. The latter involves drug delivery to a specific site based on molecular recognition. The most common approach conjugates targeting ligands to the nanoparticles. The targeting ligands enhance the interaction between nanoparticles and receptors at the target cell site, increasing local drug concentration. Many ligands can be conjugated to the nanoparticles described herein, including antibodies, transferrin receptor, folate receptors, and a wide range of biomolecules, as discussed herein.

Examples of molecules targeting extracellular matrix ("ECM") include glycosaminoglycan ("GAG") and collagen. The outer surface of the particles that have a carboxy functional group can be linked to Pathogen-associated molecular patterns (PAMPs) that have a free amine terminus. The PAMPs target Toll-like Receptors (TLRs) on the surface of the cells or tissue, or signals the cells or tissue internally, thereby potentially increasing uptake. PAMPs conjugated to the particle surface or included in the particles can include: unmethylated CpG DNA (bacterial), double-stranded RNA (viral), lipopolysaccharide (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic)acid (bacterial), lipoteichoic acid (bacterial) or imidazoquinolines (synthetic).

Lectins can also be used as targeting agents that can be covalently attached to the new particles to target them to the mucin and mucosal cell layers. Such lectins can be isolated from, e.g., *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius*, and *Lotus tetragonolobus*.

Several cell surface markers have been proposed as potential targets for tumor-homing therapeutics, including, for example, prostate-specific membrane antigen (PSMA), HER-2, HER-3, EGFR, and folate receptor. PSMA is a well established tumor marker, which is up-regulated in prostate cancer, particularly in advanced, hormone-independent, and metastatic disease (Ghosh and Heston, 2004, J. Cell. Biochem., 91:528-539). PSMA has been employed as a tumor marker for imaging of metastatic prostate cancer and as a target for experimental immunotherapeutic agents. PSMA is the molecular target of ProstaScint®, a monoclonal antibody-based imaging agent approved for diagnostic imaging of prostate cancer metastases. J591, a de-immunized monoclonal antibody that targets the external domain of PSMA, has been evaluated clinically as an agent for radioimmunotherapy and radioimmunoimaging. Radiolabeled J591 is reported to accurately target prostate cancer metastases in bone and soft tissue and to display anti-tumor activity. Interestingly, PSMA is differentially expressed at high levels on the neovasculature of most non-prostate solid tumors, including breast and lung cancers, and the clinical feasibility of PSMA targeting for non-prostate cancers was recently demonstrated in two distinct clinical trials (Morris et al., 2007, Clin. Cancer Res., 13:2707-13; Milowsky et al., 2007, J. Clin. Oncol., 25:540-547). The highly restricted presence of PSMA on prostate cancer cells and non-prostate solid tumor neovasculature makes it an attractive target for delivery of cytotoxic agents to most solid tumors.

Additional targeting agents are described in WO 2008/124632, which is incorporated herein by reference in its entirety. Other targeting moieties known or to be developed in the art are contemplated for use with the present disclosure.

Active Agents

The particles described herein can include one or more active agents. The active agents selected can be suitable for use in a wide variety of applications and include proteins, peptides, sugars, lipids, steroids, DNA, RNA, small molecule drugs, and prodrugs of any of agents described herein. As used herein, a prodrug is a pharmacological substance that is metabolized in vivo into a pharmaceutically active form. In some cases, the prodrug is pharmaceutically inactive or significantly less active than the pharmaceutically active form.

In some embodiments, the active agent is a small molecule drug. The term "small molecule" is art-recognized and refers to a composition which has a molecular weight of less than about 2000 g/mole, less than about 1500 g/mole, less than about 1000 g/mole, less than about 800 g/mole, less than about 700 g/mole, less than about 600 g/mole, less than about 500 g/mole, less than about 400 g/mole, less than about 300 g/mole, less than about 200 g/mole, less than about 100 g/mole, or less. Those of ordinary skill in the art will be able to determine if a small molecule drug is suitable to be functionalized with a polymer, e.g., a polymer having pendant functional groups.

Other examples of active agents include, but are not limited to, antimicrobial agents, analgesics, anti-inflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable active agents include contraceptives and vitamins as well as micro- and macronutrients. Still other examples include antiinfectives such as antibiotics and antiviral agents; analgesics and analgesic combinations; anorexics; antihelminthics; antiarthritics; antiasthmatic agents; anticonvulsants; antidepressants; antidiuretic agents; antidiarrleals; antihistamines; anti-inflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Suitable chemotherapeutic drugs can be divided into the following classes: alkylating agents, antimetabolites, anthracyclines, plant alkaloids, topoisomerase inhibitors, monoclonal antibodies, and other anti-tumor agents. In addition to the chemotherapeutic drugs described above, namely doxorubicin, paclitaxel, other suitable chemotherapy drugs include tyrosine kinase inhibitor imatinib mesylate (Gleevec® or Glivec®), cisplatin, carboplatin, oxaliplatin, mechloethamine, cyclophosphamide, chlorambucil, azathioprine, mercaptopurine, pyrimidine, vincristine, vinblastine, vinorelbine, vindesine, podophyllotoxin (L01CB), etoposide, docetaxel, topoisomerase inhibitors (L01CB and L01XX) irinotecan, topotecan, amsacrine, etoposide, etoposide phosphate, teniposide, dactinomycin, and monoclonal antibodies, such as trastuzumab (Herceptin®), cetuximab, bevacizumab and rituximab (Rituxan®), among others. Additional exemplary active agents include poly (ADP-ribose) polymerase (PARP) inhibitors, survivin inhibitors, estradiol, and dichloroacetate.

In certain embodiments, the particles can include lovastatin, a cholesterol lowering and heart disease active agent, which can be included within the nanoparticles described herein. In another aspect, a suitable active agent included in core of the particle is Phenytoin, an anticonvulsant agent (marketed as Dilantin®) in the USA and as Epanutin® in the UK by Pfizer, Inc). Antibiotics can be incorporated into the particle, such as vancomycin, which is frequently used to treat infections, including those due to methicillin resistant staph aureus (MRSA). The particle optionally includes cyclosporin, a lipophilic drug that is an immunosuppressant agent, widely used post-allogeneic organ transplant to reduce the activity of the patient's immune system and the risk of organ rejection (marketed by Novartis under the brand names Sandimmune®, the original formulation, and Neoral® for the newer microemulsion formulation). Particles comprising cyclosporine can be used in topical emulsions for treating keratoconjunctivitis sicca, as well. In this regard, particles with multifunctional surface domains incorporating such drugs can be designed to deliver equivalent dosages of the various drugs directly to the cancer cells, thus potentially minimizing the amount delivered generally to the patient and minimizing collateral damage to other tissues.

In certain specific aspects, the particles of the present disclosure include one or more of: non-steroidal anti-inflammatory agents (NSAIDs), analgesics, cyclooxygenase (e.g., COX-I and II) inhibitors, and the like. For example, indomethacin is a NSAID suitable for incorporation into a nanoparticle of the disclosure.

Other active agents that can be used as therapeutic agents are described in WO 2008/124632, which is incorporated herein by reference in its entirety.

Exemplary hydrophilic active agents include cisplatin, carboplatin, mitaplatin, oxaliplatin, or irinotecan, and derivatives or prodrugs thereof. Exemplary hydrophobic active agents include paclitaxel, docetaxel, gefitinib, tubacin, or combretastatin, and derivatives or prodrugs thereof.

In certain embodiments, an active agent (e.g., a hydrophobic active agent) is selected from acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eprosartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenyloin, frovatriptan, fuirazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremitfene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, zopiclone, pharmaceutically acceptable salts, isomers, and derivatives thereof, and mixtures thereof.

In certain embodiments, an active agent (e.g., an antiproliferative or chemotherapeutic agent) is selected from Abarelix, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alpha-2a, Interferon Alpha-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

In certain embodiments, an agent is a DNA plasmid, a short interfering RNA (siRNA), a micro RNA (miRNA), a short hairpin RNA (shRNA), an antisense RNA, Piwi-interacting RNA (piRNA), or other RNA-based therapeutic, an oligopeptide, a peptide, a monoclonal antibody, a cytokine, or other protein therapeutic.

In certain embodiments the agent comprises a growth factor or a cytokine such as leptin, sortilin, transglutaminase, prostaglandin E, 1,25-dihydroxyvitamin D3, ascorbic acid, β-glycerol phosphate, TAK-778, statins, interleukins such as IL-3 and IL-6, growth hormone, steel factor (SF), activin A (ACT), retinoic acid (RA), epidermal growth factor (EGF), bone morphogenetic proteins (BMP), platelet derived growth factor (PDGF), hepatocyte growth factor, insulin-like growth factors (IGF) I and II, hematopoietic growth factors, peptide growth factors, erythropoietin, interleukins, tumor necrosis factors, interferons, colony stimulating factors, heparin binding growth factor (HBGF), alpha or beta transforming growth factor (α or β-TGF) such as TGF-β1, fibroblast growth factors, vascular endothelium growth factor (VEGF), nerve growth factor (NGF) and muscle morphogenic factor (MMP).

In one aspect, the present invention provides compositions and methods that enable multiple active agents with varying chemical properties to be administered to patients, e.g., simultaneously in a safe, effective, and controlled manner. Combining multiple active agents into a single particle also allows for targeting of the active agents to specific cellular targets, e.g., tumor cells. Indeed, the treatment efficacy of many traditional combination therapies (e.g., cancer treatments that use two or more drugs) is often limited because the dose-limiting toxicities (DLTs) of the individual drugs are lower when the two drugs are administered in combination than when they are administered individually. In such cases, the dose of each drug needs to be reduced in the combination therapy, thereby reducing the individual drug contributions to overall treatment efficacy. In addition, this hampers the opportunities for identifying novel synergisms. In some embodiments of the present invention, this problem is solved by using an active agent encapsulated by a biodegradable polymer as one or more of the combination therapeutics. Because these particles deliver their drugs in a targeted manner, they have higher dose-limiting toxicities than the drugs themselves. By using a conjugate as one or more of the combination therapeutics one can therefore increase the dose of one or more of the drugs in the combination. In one embodiment, two or more conjugates that each carry different drugs are administered in combination. In one embodiment, a conjugate is administered with one or more non-conjugated drugs. In any of these embodiments it is to be understood that one can increase the dose of just one or several drugs in the combination (e.g., one or both drugs in a combination of two drugs). It is also to be understood that one can increase the dose of a drug which is conjugated and/or the dose of a drug which is non-conjugated.

The methods and compositions of the present invention are in no way limited to specific drugs, specific drug combinations, or specific diseases, but certain combinations disclosed herein can provide beneficial and/or synergistic results.

For example, and without limitation, certain agents with known synergies can be combined into a single particle. For example, paclitaxel or docetaxel with gefitinib has been shown to have a strong synergistic effect in breast cancer MCF7/ADR cells; oxaloplatin and irinotecan have a synergistic anticancer effect in AZ-521 and NUGC-4 cells; and paclitaxel and tubacin synergistically enhance tubulin acetylation. Additionally, combretastatin or another agent that blocks neovascularization can be incorporated into the delivery compositions, including delivery compositions that include targeting agents specific for PSMA. Other combinations that can be incorporated can be found, e.g., in Jia et al., 2009, Nat. Rev. Drug. Discov., 8:111-128, and include DL-cycloserine and epigallocatechin gallate; paclitaxel and NU6140; gefitinib and taxane; gefitinib and PD98059; AZT and non-nucleoside HIV-1 reverse transcriptase inhibitors; aplidin and cytarabine; gefitinib and ST1926; sildenafil and iloprost; dexmedetomidine and ST-91; mycophenolate mofetil and mizoribine; paclitaxel and discodermolide;

ampicillin and daptomycin; candesartan-cilexetil and ramipril; diazoxide and dibutyryl-cGMP; propofol and sevoflurane; ampicillin and imipenem; artemisinin and curcumin; doxorubicin and trabectedin; and azithromycin and imipenem. Jia et al., Nat. Rev. Drug. Discov., 8:111-128, is incorporated herein by reference in its entirety For example, and without limitation, certain metastatic breast cancers are currently treated with a combination of cyclophosphamide, methotrexate and fluorouracil (CMF) or a combination of cyclophosphamide, doxorubicin and fluorouracil (CAF). Thus, in one embodiment, two or three of the above agents in these combination therapies could be administered in a single particle.

Bladder, head and neck and endometrial cancers could similarly be treated by administering two or more of the individual drugs in M-VAC (methotrexate, vinblastin, adriamycin, cisplatin) or CMV (cisplatin, methotrexate, vinblastin) in a single particle.

One of ordinary skill will recognize variations on these embodiments for other traditional combination therapies (e.g., without limitation, any of those described in "Combination Cancer Therapy: Modulators and Potentiators", Ed. by Schwartz, Humana Press, 2004; "Combination Therapy of AIDS", Ed. by DeClerq et al., Birkhauser, 2004; etc.).

In some embodiments, an active agent is a nucleic acid, e.g., a nucleic acid that directs exogenous expression of a gene, an inhibitory nucleic acid, or an immunostimulatory nucleic acid. Nucleic acids can be associated with the aqueous core of the particles disclosed herein or adsorbed on the surface of the particles. In some embodiments, the portion of the particle in contact with the nucleic acid includes a positively charged moiety.

In certain embodiments, a nucleic acid can direct expression of an exogenous gene, e.g., a sequence encoding a protein or a regulatory nucleic acid. The nucleic acid can be a plasmid or other expression construct, and can include one or more promoters or expression regulatory elements (e.g., enhancers or repressors). The nucleic acid can encode a therapeutic agent (e.g., a therapeutic polypeptide), a diagnostic agent (e.g., a fluorescent [e.g., GFP] or enzymatically detectable [e.g., beta-galactosidase] polypeptide), or an immunomodulatory agent (e.g., an antigenic polypeptide).

Inhibitory nucleic acids, e.g., siRNA, miRNA, piRNA, antisense, ribozymes, or aptamers, can also be used as active agents.

RNA interference (RNAi) is a process whereby double-stranded RNA (dsRNA) induces the sequence-specific regulation of gene expression in animal and plant cells and in bacteria (Aravin and Tuschl, FEBS Lett. 26:5830-5840 (2005); Herbert et al., Curr. Opin. Biotech. 19:500-505 (2008); Hutvagner and Zamore, Curr. Opin. Genet. Dev.: 12, 225-232 (2002); Sharp, Genes Dev., 15:485-490 (2001); Valencia-Sanchez et al. Genes Dev. 20:515-524 (2006)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411: 494-498 (2001)), by microRNA (miRNA), functional small-hairpin RNA (shRNA), or other dsRNAs which are expressed in vivo using DNA templates with RNA polymerase II or III promoters (Zeng et al., Mol. Cell 9:1327-1333 (2002); Paddison et al., Genes Dev. 16:948-958 (2002); Denti, et al., Mol. Ther. 10:191-199 (2004); Lee et al., Nature Biotechnol. 20:500-505 (2002); Paul et al., Nature Biotechnol. 20:505-508 (2002); Rossi, Human Gene Ther. 19:313-317 (2008); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Scherer et al., Nucleic Acids Res. 35:2620-2628 (2007); Sui et al., Proc. Natl. Acad. Sci. USA 99(6):5515-5520 (2002).)

The methods described herein can use, e.g., dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro or in vivo, e.g., shRNA, from a DNA template. The dsRNA molecules can be designed using any method known in the art. Negative control siRNAs should not have significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The methods described herein can use both siRNA and modified siRNA derivatives, e.g., siRNAs modified to alter a property such as the specificity and/or pharmacokinetics of the composition, for example, to increase half-life in the body, e.g., crosslinked siRNAs. Thus, the invention includes methods of administering siRNA derivatives that include siRNA having two complementary strands of nucleic acid, such that the two strands are crosslinked. The oligonucleotide modifications include, but are not limited to, 2'-O-methyl, 2'-fluoro, 2'-O-methyoxyethyl and phosphorothioate, boranophosphate, 4'-thioribose. (Wilson and Keefe, Curr. Opin. Chem. Biol. 10:607-614 (2006); Prakash et al., J. Med. Chem. 48:4247-4253 (2005); Soutschek et al., Nature 432:173-178 (2004))

In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The inhibitory nucleic acid compositions can be unconjugated or can be conjugated to another moiety of the particle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles). The inhibitory nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using 3H, 32P, or other appropriate isotope.

siRNA duplexes can be expressed within cells from recombinant DNA constructs, including mammalian Pol II and III promoter systems (e.g., H1, U1, or U6/snRNA promoter systems (Denti et al. (2004), supra; Tuschl (2002), supra); capable of expressing functional double-stranded siRNAs (Bagella et al., J. Cell. Physiol. 177:206-213 (1998); Lee et al. (2002), supra; Miyagishi et al. (2002), supra; Paul et al. (2002), supra; Scherer et al. (2007), supra; Yu et al. (2002), supra; Sui et al. (2002), supra).

In another embodiment, siRNAs can be expressed in a miRNA backbone which can be transcribed by either RNA Pol II or III. MicroRNAs are endogenous noncoding RNAs of approximately 22 nucleotides in animals and plants that can post-transcriptionally regulate gene expression (Bartel, Cell 116:281-297 (2004); Valencia-Sanchez et al., Genes & Dev. 20:515-524 (2006)). One common feature of miRNAs is that they are excised from an approximately 70 nucleotide precursor RNA stem loop by Dicer, an RNase III enzyme, or a homolog thereof. By substituting the stem sequences of the miRNA precursor with the sequence complementary to the target mRNA, a vector construct can be designed to produce siRNAs to initiate RNAi against specific mRNA targets in mammalian cells. When expressed by DNA vectors containing polymerase II or III promoters, miRNA designed hairpins can silence gene expression (McManus (2002), supra; Zeng (2002), supra).

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage, destabilization, and/or translation inhibition destruction. In this fashion, an mRNA to be targeted by the siRNA generated from the engineered RNA precursor can be depleted from the cell or organism, leading to a decrease in the concentration of the protein encoded by that mRNA in the cell or organism.

An "antisense" nucleic acid can include a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof (for example, the coding region of a target gene). In another embodiment, the antisense nucleic acid molecule is antisense to a "noncoding region" of the coding strand of a nucleotide sequence encoding the selected target gene (e.g., the 5' and 3' untranslated regions).

An antisense nucleic acid can be designed such that it is complementary to the entire coding region of a target mRNA but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual β-units, the strands run parallel to each other (Gaultier et al., Nucleic Acids. Res. 15:6625-41 (1987)). The antisense nucleic acid molecule can also comprise a 2'-O-methylribonucleotide (Inoue et al. Nucleic Acids Res. 15:6131-48 (1987)), 2'-O-methoxyethylribonucleotide, locked nucleic acid, ethylene-bridged nucleic acid, oxetane-modified ribose, peptide nucleic acid, or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243:209-14 (2002); Iversen, Curr. Opin. Mol. Ther. 3:235-238 (2001); Summerton, Biochim. Biophys. Acta. 1489: 141-58 (1999).

Target gene expression can be inhibited by targeting nucleotide sequences complementary to a regulatory region, e.g., promoters and/or enhancers) to form triple helical structures that prevent transcription of the target gene in target cells. See generally, Helene, C. Anticancer Drug Des. 6:569-584 (1991); Helene, C. Ann. N.Y. Acad. Sci. 660:27-36 (1992); and Maher, Bioassays 14:807-815 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target-protein encoding nucleic acid can include one or more sequences complementary to the nucleotide sequence of a target cDNA disclosed herein, and a sequence having known catalytic sequence responsible for mRNA cleavage (see U.S. Pat. No. 5,093,246 or Haseloff and Gerlach Nature 334: 585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-18 (1993).

An inhibitory nucleic acid can target a protein tyrosine phosphatase (PTP-1B) gene or a MAP kinase gene, such as ERK1, ERK2, JNK1, JNK2, or p38. In some embodiments, these inhibitory nucleic acids are used to silence genes in a fibroblast cell.

An inhibitory nucleic acid can target an MDR, Myc, Myb, c-Myc, N-Myc, L-Myc, c-Myb, a-Myb, b-Myb, v-Myb, cyclin D1, Cyclin D2, cyclin E, CDK4, cdc25A, CDK2, or CDK4 gene. In some embodiments, these inhibitory nucleic acids are used to silence genes in an epithelial cell or mesodermal cell.

An inhibitory nucleic acid can target a G72 or DAAO gene. In some embodiments, these inhibitory nucleic acids are used to silence genes in a neural cell.

An inhibitory nucleic acid can target a gene of the telomerase pathway, such as a TERT or TR/TERC. In some embodiments, these inhibitory nucleic acids are used to silence genes in a keratinocyte.

An inhibitory nucleic acid can target a cytokine (e.g., interleukin or chemokine) gene, such as IL-1, IL-2, IL-5, IL-8, IL-10, IL-15, IL-16, IL-17, IL-18, or TNF-alpha, or a cytokine (e.g., interleukin or chemokine) receptor gene, such as CCR3, the common beta chain of IL-3/5 receptor, or a chromosomal translocation, such as BCR-ABL, TEL-AML-1, EWS-FLI1, EWS-ERG, TLS-FUS, PAX3-FKHR, or AML-ETO. In some embodiments, these inhibitory nucleic acids are used to silence genes in a lymphoma or a leukemia cell.

An inhibitory nucleic acid can target a cluster of differentiation protein, such as CD40, CD49d (VLA-4), CD54 (ICAM-1), CD80, or CD86. In some embodiments, the inhibitory nucleic acids are used to silence gens in a leukocyte or endothelial cell.

An inhibitory nucleic acid can target a GRB2 associated binding protein. In some embodiments, these inhibitory nucleic acids are used to silence genes in a mast cell.

An inhibitory nucleic acid can target a growth factor or growth factor receptor, such as a TGFbeta or TGFbeta Receptor; PDGF or PDGFR; VEGF or VEGFr1, VEGFr2, or VEGFr3; or IGF-1R, DAF-2, or 1nR. In other embodiments, the inhibitory nucleic acid agent targets PRL1, PRL2, PRL3, p53, protein kinase C (PKC), PKC receptor, protein kinase A type 1 regulatory alpha subunit (PKA R1α), MDR1, TERT, TR/TERC, cyclin D1, NF-KappaB, REL-A, REL-B, PCNA, CHK-1, H-Ras, c-Raf, Hsp27, survivin, eIF-4E, clusterin, ribonucleotide reductase, XIAP, DNA methyltransferase, cyp 3A4, Hif-1α, c-fos, jun, or BCL-2. In some embodiments, these inhibitory nucleic acids are used to silence genes in an adherent tumor cell line.

An inhibitory nucleic acid can target a gene encoding an anti-apoptotic protein, e.g., a Bcl-2 family protein (e.g., Bcl-2, Bcl-xL, Bcl-w, Mcl-1, CED-9, A1, or Bfl-1), PHB1, GSTπ (Patel et al., 2010, Proc. Natl. Acad. Sci. USA, 107:2503-08), MSK1 (Fujita et al., 2010, J. Biol. Chem. 285:19076-84), Rev3, or Rev1 (Xie et al., 2010, Proc. Natl. Acad. Sci. USA, 107:20792-97). In some embodiments, an inhibitory nucleic acid targeting MSK1 is miR-148a (Fujita et al., 2010, J. Biol. Chem. 285:19076-84).

An inhibitory nucleic acid can target a gene encoding a protein involved in drug resistance, e.g., Bcl-2 protein, P-glycoprotein (P-gp), multidrug resistance 2 (MDR2), a cyclooxygenase (e.g., COX-1 or COX-2), Ral binding protein (RalBP-1/RLIP76) (Awasthi et al., 2007, Curr. Drug Metab., 8:315-323), breast cancer resistance protein (BCRP) (Yue et al., 2009, Mol. Pharm., 6:134-143), or a multidrug resistance-associated protein (e.g., MRP1, MRP2, MRP3, MRP4, MRP5, MRP6, MRP7, MRP8, or MRP9). Drug resistance proteins are reviewed in Zhou et al., 2008, Curr. Med. Chem., 15:1981-2039; Lee, 2010, Methods Mol. Biol., 596:325-340; Stavrovskaya et al., 2008, Biochemistry (Mosc.), 73:592-604; and Fletcher et al., 2010, Nature Rev. Cancer, 10:147-156. In some embodiments, an inhibitory nucleic acid targeting a gene encoding a protein involved in drug resistance is co-encapsulated with an inhibitory nucleic acid targeting a gene encoding an anti-apoptotic protein (see FIG. 12). In some embodiments, an inhibitory nucleic acid targeting a gene encoding a protein involved in drug resistance is co-encapsulated with a drug that the protein provides resistance to. Exemplary drug classes, drugs, and associated resistance proteins are shown in the table below.

TABLE

Drugs and associated resistance proteins

| Drug Class | Exemplary Drugs | Resistance Proteins |
| --- | --- | --- |
| Anthracyclines | doxorubicin, daunorubicin, epirubicin, idarubicin | P-gp, MRP1, MRP2, BCRP |
| Epipodophyllotoxins | etoposide, teniposide | P-gp, MRP1, MRP2, BCRP |
| Vinca alkaloids | vincristine, vinblastine, vinorelbine | P-gp, MRP1, MRP2 |
| Taxanes | paclitaxel, docetaxel | P-gp, MRP2 |
| Kinase inhibitors | imatinib, flavopyridol | P-gp, MRP2, BCRP |
| Others | mitoxantrone, tamoxifen, mitomycin, actinomycin D, methotrexate | P-gp, MRP1, MRP2, BCRP |

An inhibitory nucleic acid can target an exogenous gene of a genetically modified cell. An exogenous gene can be, for example, a viral or bacterial gene that derives from an organism that has invaded or infected the cell, or the exogenous gene can be any gene introduced into the cell by natural or artificial means, such as by a genetic recombination event. An inhibitory nucleic acid can target a viral gene or regulatory sequence, for example, such as a hepatitis viral gene or internal ribosome entry site (e.g., from HAV, HBV, or HCV), an immunodeficiency virus (e.g., human immunodeficiency virus) gene (e.g., gag, env), a cytomegalovirus gene (e.g., immediate early (IE)). Alternatively, or in addition, the inhibitory nucleic acid can silence a reporter gene, such as GFP or beta galactosidase and the like. These inhibitory nucleic acids can be used to silence exogenous genes in an adherent tumor cell line.

In some embodiments, the particles are formulated for immunomodulation (e.g., vaccination) by incorporating one or more immunogens and/or immunostimulatory substances (e.g., adjuvants). In some instances, the immunostimulatory substances can be immunostimulatory nucleic acids.

Two classes of nucleic acids, namely 1) bacterial-like DNA that contains immunostimulatory sequences, in particular unmethylated CpG dinucleotides within specific flanking bases (referred to as CpG motifs) and 2) double-stranded RNA synthesized by various types of viruses represent important members of the microbial components that enhance immune responses. Synthetic double stranded (ds) RNA such as polyinosinic-polycytidylic acid (poly I:C) are capable of inducing dendritic cells to produce proinflammatory cytokines and to express high levels of costimulatory molecules.

A series of studies by Tokunaga and Yamamoto et al. has shown that bacterial DNA or synthetic oligodeoxynucleotides induce human PBMC and mouse spleen cells to produce type I interferon (IFN) (reviewed in Yamamoto et al., Springer Semin Immunopathol. 22:11-19, 2000). Poly (I:C) was originally synthesized as a potent inducer of type I IFN but also induces other cytokines such as IL-12.

Certain ribonucleic acids encompass polyinosinic-polycytidylic acid double-stranded RNA (poly I:C). Ribonucleic acids and modifications thereof as well as methods for their production have been described by Levy, H. B (Methods Enzymol. 1981, 78:242-251), DeClercq, E (Methods Enzymol. 1981, 78:227-236) and Torrence, P. F. (Methods Enzymol. 1981; 78:326-331) and references therein. Ribonucleic acids can be isolated from organisms. Ribonucleic acids also encompass further synthetic ribonucleic acids, in particular synthetic poly (I:C) oligonucleotides that have been rendered nuclease resistant by modification of the phosphodiester backbone, in particular by phosphorothioate modifications. In a further embodiment the ribose backbone of poly (I:C) is replaced by a deoxyribose. Those skilled in the art know procedures how to synthesize synthetic oligonucleotides.

In another embodiment of the invention molecules that activate toll-like receptors (TLR) are enclosed. Ten human toll-like receptors are known to date. They are activated by a variety of ligands. TLR2 is activated by peptidoglycans, lipoproteins, lipoteichoic acid and Zymosan; TLR3 is activated by double-stranded RNA such as poly (I:C); TLR4 is activated by lipopolysaccharide, lipoteichoic acids and taxol; TLR5 is activated by bacterial flagella, especially the flagellin protein; TLR6 is activated by peptidoglycans, TLR7 is activated by imiquimoid and imidazoquinoline compounds, such as R418 and R848, TLR8 is activated by R848, and TLR9 is activated by bacterial DNA, in particular CpG DNA. TLR1 recognizes peptidoglycan and triacyl lipoproteins in combination with TLR2 as a heterodimer. The above list of ligands is not exhaustive and further ligands are within the knowledge of the person skilled in the art.

In some embodiments, an unmethylated CpG-containing oligonucleotide comprises the sequence:

5'-$X_1 X_2 CGX_3 X_4$-3' wherein $X_1$, $X_2$, $X_3$ and $X_4$ are any nucleotide. In addition, the oligonucleotide can comprise about 6 to about 100,000 nucleotides, e.g., about 6 to about 2000 nucleotides, e.g., about 20 to about 2000 nucleotides, e.g., about 20 to about 300 nucleotides. In addition, the oligonucleotide can comprise more than 100 to about 2000 nucleotides, e.g., 100 to about 1000 nucleotides, e.g., than 100 to about 500 nucleotides.

In certain embodiments, a CpG-containing oligonucleotide contains one or more phosphorothioate modifications of the phosphate backbone. For example, a CpG-containing oligonucleotide having one or more phosphate backbone modifications or having all of the phosphate backbone modified and a CpG-containing oligonucleotide wherein one, some or all of the nucleotide phosphate backbone modifications are phosphorothioate modifications are included within the scope of the present invention.

The CpG-containing oligonucleotide can also be recombinant, genomic, synthetic, cDNA, plasmid-derived and single or double stranded. For use in the instant invention, the nucleic acids can be synthesized de novo using any of a number of procedures well known in the art. For example, the b-cyanoethyl phosphoramidite method (Beaucage, S. L., and Caruthers, M. H., Tet. Let. 22:1859 (1981); nucleoside H-phosphonate method (Garegg et al., Tet. Let. 27:4051-4054 (1986); Froehler et al., Nucl. Acid. Res. 14:5399-5407 (1986); Garegg et al., Tet. Let. 27:4055-4058 (1986), Gaffney et al., Tet. Let. 29:2619-2622 (1988)). These chemistries can be performed by a variety of automated oligonucleotide synthesizers available in the market. Alternatively, CpGs can be produced on a large scale in plasmids, (see Sambrook, T., et al., "Molecular Cloning: A Laboratory Manual," Cold Spring Harbor laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases.

The immunostimulatory substances, the immunostimulatory nucleic acids as well as the unmethylated CpG-containing oligonucleotide can be incorporated in the particles by any way known is the art provided the composition enhances an immune response in an animal. For example, the oligonucleotide can be bound either covalently or non-covalently to a component of the particle. In addition, the particle can enclose, fully or partially, the immunostimulatory substances, the immunostimulatory nucleic acids as well as the unmethylated CpG-containing oligonucleotide.

One contemplated use for the compositions of the invention is to activate dendritic cells for the purpose of enhancing a specific immune response against antigens. The immune response can be enhanced using ex vivo or in vivo techniques. The ex vivo procedure can be used on autologous or heterologous cells, but is typically used on autologous cells. In certain embodiments, the dendritic cells are isolated from peripheral blood or bone marrow, but can be isolated from any source of dendritic cells. Ex vivo manipulation of dendritic cells for the purposes of cancer immunotherapy have been described in several references in the art, including Engleman, E. G., Cytotechnology 25:1 (1997); Van Schooten, W., et al., Molecular Medicine Today, June, 255 (1997); Steinman, R. M., Experimental Hematology 24:849 (1996); and Gluckman, J. C., Cytokines, Cellular and Molecular Therapy 3:187 (1997).

The dendritic cells can also be contacted with the inventive compositions using in vivo methods. To accomplish this, the CpGs are administered in combination with the particles that include an antigen directly to a subject in need of immunotherapy. In some embodiments, it is preferred that the particles be administered in the local region of the tumor, which can be accomplished in any way known in the art, e.g., direct injection into the tumor.

The present invention is applicable to a wide variety of antigens. In some embodiments, the antigen is a protein, polypeptide or peptide. In other embodiments the antigen is DNA. The antigen can also be a lipid, a carbohydrate, or an organic molecule, in particular a small organic molecule such as nicotine. Exemplary antigens are disclosed in US 2003/0099668 and WO 03/024481, both of which are incorporated herein by reference.

Antigens of the invention can be selected from the group consisting of the following: (a) polypeptides suited to induce an immune response against cancer cells; (b) polypeptides suited to induce an immune response against infectious diseases; (c) polypeptides suited to induce an immune response against allergens; (d) polypeptides suited to induce an immune response in farm animals or pets; and (e) fragments (e.g., a domain) of any of the polypeptides set out in (a)-(d).

Exemplary antigens include those from a pathogen (e.g. virus, bacterium, parasite, fungus) and tumors (especially tumor-associated antigens or "tumor markers"). Other exemplary antigens include autoantigens.

In one specific embodiment of the invention, the antigen or antigenic determinant is one that is useful for the prevention of infectious disease. Such treatment will be useful to treat a wide variety of infectious diseases affecting a wide range of hosts, e.g., human, cow, sheep, pig, dog, cat, other mammalian species and non-mammalian species as well. Treatable infectious diseases are well known to those skilled in the art, and examples include infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc. Thus, antigens or antigenic determinants selected for the compositions of the invention will be well known to those in the medical art; examples of antigens or antigenic determinants include the following: the HIV antigens gp140 and gp160; the influenza antigens hemagglutinin, M2 protein and neuraminidase, Hepatitis B surface antigen or core and circumsporozoite protein of malaria or fragments thereof.

As discussed above, antigens include infectious microbes such as viruses, bacteria and fungi and fragments thereof, derived from natural sources or synthetically. Infectious viruses of both human and non-human vertebrates include retroviruses, RNA viruses and DNA viruses. The group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian mycloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-T1, simian T-cell leukemia virus (STLV), and bovine leukemia virus (BLV). The foamy viruses include human foamy virus (HFV), simian foamy virus (SFV) and bovine foamy virus (BFV).

Polypeptides of bacterial pathogens include, but are not limited to, an iron-regulated outer membrane protein (IROMP), an outer membrane protein (OMP), and an A-protein of *Aeromonis salmonicida* which causes furunculosis, p57 protein of *Renibacterium salmoninarum* which causes bacterial kidney disease (BKD), major surface associated antigen (msa), a surface expressed cytotoxin (mpr), a surface expressed hemolysin (ish), and a flagellar antigen of *Yersiniosis*; an extracellular protein (ECP), an iron-regulated outer membrane protein (IROMP), and a structural protein of *Pasteurellosis*; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of *Ichthyophthirius*; and a structural and regulatory protein of *Cytophaga columnari*; and a structural and regulatory protein of Rickettsia.

In another aspect of the invention, there are provided vaccine compositions suitable for use in methods for preventing and/or attenuating diseases or conditions that are caused or exacerbated by "self" gene products (e.g., tumor necrosis factors). Thus, vaccine compositions of the invention include compositions that lead to the production of antibodies that prevent and/or attenuate diseases or conditions caused or exacerbated by "self" gene products. Examples of such diseases or conditions include graft versus host disease, IgE-mediated allergic reactions, anaphylaxis, adult respiratory distress syndrome, Crohn's disease, allergic asthma, acute lymphoblastic leukemia (ALL), non-Hodgkin's lymphoma (NHL), Graves' disease, systemic lupus erythematosus (SLE), inflammatory autoimmune diseases, myasthenia gravis, immunoproliferative disease lymphadenopathy (IPL), angioimmunoproliferative lymphadenopathy (AIL), immunoblastive lymphadenopathy (IBL), rheumatoid arthritis, diabetes, prion diseases, multiple sclerosis, Alzheimer disease and osteoporosis.

In related specific embodiments, compositions of the invention are an immunotherapeutic that can be used for the treatment and/or prevention of allergies, cancer or drug addiction.

The selection of antigens or antigenic determinants for compositions and methods of treatment for cancer would be known to those skilled in the medical arts treating such disorders (see Renkvist et al., Cancer. Immunol. Immunother. 50:3-15 (2001) which is incorporated by reference), and such antigens or antigenic determinants are included within the scope of the present invention. Representative examples of such types of antigens or antigenic determinants include the following: Her2 (breast cancer); GD2 (neuroblastoma); EGF-R (malignant glioblastoma); CEA (medullary thyroid cancer); CD52 (leukemia); human melanoma protein gp100; human melanoma protein gp100 epitopes such as amino acids 154-162 (KTWGQYWQV; SEQ ID NO:5), 209-217 (ITDQVPFSV; SEQ ID NO:6), 280-288 (YLEPGPVTA; SEQ ID NO:7), 457-466 (LLDGTATLRL; SEQ ID NO:8) and 476-485 (VLYRYGSFSV; SEQ ID NO:9); human melanoma protein melan-A/MART-1; human melanoma protein melan-A/MART-1 epitopes such as amino acids 27-35 (AAGIGILTV; SEQ ID NO:10) and 32-40 (ILTVILGVL; SEQ ID NO:11); tyrosinase and tyrosinase related proteins (e.g., TRP-1 and TRP-2); tyrosinase epitopes such as amino acids 1-9 (MLLAVLYCL; SEQ ID NO:12) and 369-377 (YMDGTMSQV; SEQ ID NO:13); NA17-A nt protein; NA17-A nt protein epitopes such as amino acids 38-64 (VLPDVFIRC; SEQ ID NO:14); MAGE-3 protein; MAGE-3 protein epitopes such as amino acids 271-279 (FLWGPRALV; SEQ ID NO:15); other human tumors antigens, e.g. CEA epitopes such as amino acids 571-579 (YLSGANLNL; SEQ ID NO:16); p53 protein; p53 protein epitopes such as amino acids 65-73 (RMPEAAPPV; SEQ ID NO:17), 149-157 (STPPPGTRV; SEQ ID NO:18) and 264-272 (LLGRNSFEV; SEQ ID NO:19); Her2/neu epitopes such as amino acids 369-377 (KIFGSLAFL; SEQ ID NO:20) and 654-662 (IISAVVGIL; SEQ ID NO:21); NY-ESO-1 peptides 157-165 and 157-167, 159-167; HPV16 E7 protein; HPV16 E7 protein epitopes such as amino acids 86-93 (TLGIVCPI; SEQ ID NO:22); as well as fragments of each which can be used to elicit immunological responses.

The selection of antigens or antigenic determinants for compositions and methods of treatment for drug addiction, in particular recreational drug addiction, would be known to those skilled in the medical arts treating such disorders. Representative examples of such antigens or antigenic determinants include, for example, opioids and morphine derivatives such as codeine, fentanyl, heroin, morphium and opium; stimulants such as amphetamine, cocaine, MDMA (methylenedioxymethamphetamine), methamphetamine, methylphenidate and nicotine; hallucinogens such as LSD, mescaline and psilocybin; as well as cannabinoids such as hashish and marijuana.

The selection of antigens or antigenic determinants for compositions and methods of treatment for other diseases or conditions associated with self antigens would be also known to those skilled in the medical arts treating such disorders. Representative examples of such antigens or antigenic determinants are, for example, lymphotoxins (e.g. Lymphotoxin alpha (LT-alpha.), Lymphotoxin beta (LT-beta)), and lymphotoxin receptors, Receptor activator of nuclear factor kappaB ligand (RANKL), vascular endothelial growth factor (VEGF) and vascular endothelial growth factor receptor (VEGF-R), Interleukin 17 and amyloid beta peptide (Aβ1-42), TNF-alpha, MIF, MCP-1, SDF-1, Rank-L, M-CSF, Angiotensin II, Endoglin, Eotaxin, Grehlin, BLC, CCL21, IL-13, IL-17, IL-5, IL-8, IL-15, Bradykinin, Resistin, LHRH, GHRH, GIH, CRH, TRH and Gastrin, as well as fragments of each which can be used to elicit immunological responses.

In a particular embodiment of the invention, the antigen or antigenic determinant is selected from the group consisting of: (a) a recombinant polypeptide of HIV; (b) a recombinant polypeptide of Influenza virus (e.g., an Influenza virus M2 polypeptide or a fragment thereof); (c) a recombinant polypeptide of Hepatitis C virus; (d) a recombinant polypeptide of Hepatitis B virus (e) a recombinant polypeptide of Toxoplasma; (f) a recombinant polypeptide of Plasmodium falciparum; (g) a recombinant polypeptide of Plasmodium vivax; (h) a recombinant polypeptide of Plasmodium ovale; (i) a recombinant polypeptide of Plasmodium malariae; (j) a recombinant polypeptide of breast cancer cells; (k) a recombinant polypeptide of kidney cancer cells; (l) a recombinant polypeptide of prostate cancer cells; (m) a recombinant polypeptide of skin cancer cells; (n) a recombinant polypeptide of brain cancer cells; (o) a recombinant polypeptide of leukemia cells; (p) a recombinant profiling; (q) a recombinant polypeptide of bee sting allergy; (r) a recombinant polypeptide of nut allergy; (s) a recombinant polypeptide of pollen; (t) a recombinant polypeptide of house-dust; (u) a recombinant polypeptide of cat or cat hair allergy; (v) a recombinant protein of food allergies; (w) a recombinant protein of asthma; (x) a recombinant protein of *Chlamydia*; and (y) a fragment of any of the proteins set out in (a)-(x).

Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts, MF-59, and Virosomal adjuvant technology. The adjuvants can also comprise a mixture of these substances.

Imaging Agents

In some embodiments, the active agent is an imaging agent or probe. Exemplary agents include quantum dots, contrast agents, iron oxides, fluorescent moieties, and/or radioisotopes.

Contrast agents can be used with various imaging modalities, such as X-rays, computerized tomography, Magnetic Resonance Imaging (MRI), nuclear imaging or ultrasound, to enable or enhance imaging. For use in MRI, for example, the particles can include any of a number of existing or novel paramagnetic nanoparticle contrast agents. Various fluorescent moieties are known that can be incorporated into the particles disclosed herein. Fluorescent labels include near-infrared fluorophores such as Cy5, Cy5.3™, Cy5.5™, and Cy7™ fluorophores (Amersham Piscataway, N.J.), Alexa Fluor® 680, Alexa Fluor® 700, and Alexa Fluor® 750 fluorophores (Molecular Probes Eugene, Oreg.), Licor NIR™, IRDye38™, IRDye78™, and IRDye80™ fluorophores (LiCor Lincoln, Nebr.), or LaJolla Blue™ fluorophore (Diatron, Miami, Fla.), and indocyanine green and the fluorochromes disclosed in U.S. Pat. No. 6,083,875.

Radioisotopes suitable for nuclear imaging are known in the art and include, without limitation, Technetium-99m, Indium-111, and Gallium-67.

Methods of Making Particles

Delivery compositions described herein can be prepared by any emulsion method known in the art. Emulsion methods for preparing particles are reviewed in Mundargi et al., 2008, J. Control. Release, 125:193-209; Anton et al., 2008, J. Control. Release, 128:185-199; and Nakashima et al., 2000, Adv. Drug Deliv. Rev., 45:47-56, all of which are incorporated herein by reference in their entirety.

In an exemplary method, a biodegradable polymeric material is mixed with an amphiphilic compound in a water immiscible organic solvent. The biodegradable polymer can be, but is not limited to one or a plurality of the following: poly(D,L-lactic acid), poly(D,L-glycolic acid), poly(ε-caprolactone), or their copolymers at various molar ratios. The amphiphilic compound can be, but is not limited to, one or a plurality of the following: naturally derived lipids, lipid-like materials, surfactants, or synthesized compounds with both hydrophilic and hydrophobic moieties. The water immiscible organic solvent, can be, but is not limited to, one or a plurality of the following: chloroform, dichloromethane, and acyl acetate (e.g., ethyl acetate).

Separately, an active agent is dissolved in an aqueous solution optionally containing one or multiple water miscible solvents. The agent can be, but is not limited to, one or a plurality of the following: genes (e.g. DNA and RNA), proteins, antigens, chemotherapeutic drugs, imaging probes, or hydrophilic/lipophilic molecules for medical use. The water miscible solvent can be, but is not limited to: acetone, ethanol, methanol, and isopropyl alcohol. The resulting aqueous solution is then added into the water immiscible organic solution to yield a first emulsion solution by emulsification. The emulsification technique can be, but not limited to, probe sonication or homogenization.

In some embodiments, a second amphiphilic compound is dissolved in an aqueous solution optionally containing one or multiple water miscible solvents. The second amphiphilic compound can be same with or different from the first one. The second amphiphilic solution is then added into the first emulsion solution to yield a second emulsion, followed by the formation of micro/nano-particles by solvent evaporation.

In certain embodiments, a targeting molecule is chemically conjugated to the hydrophilic region of the second amphiphilic compound. This conjugate is then mixed with a certain ratio of unconjugated amphiphilic compounds in an aqueous solution containing or without containing one or more water-miscible solvents. The targeting molecule can be one or a plurality of antibodies, aptamers, peptides, sugars, small molecules, or combinations thereof. The targeting molecule can then be presented on the surface of aforementioned micro/nano-particles for targeted drug delivery.

In another embodiment, an antigen is chemically conjugated to the hydrophilic region of the second amphiphilic compound. This conjugate is then mixed with a certain ratio of unconjugated amphiphilic compounds in an aqueous solution containing or without containing one or more water-miscible solvents. The antigen molecule is one or a plurality of proteins, peptides, sugars, small molecules, or combinations thereof. The antigen molecule can then be presented on the surface of aforementioned micro/nano-particles for immune response.

In another embodiment, a second active agent is mixed with the water immiscible organic solution containing polymer and amphiphilic molecules. The agent can be, but is not limited to, one or a plurality of the following: therapeutic drugs, imaging probes, or hydrophobic or lipophilic molecules for medical use.

In the above methods, the sonication time and amplitude can be optimized for formulating particles with size scale from nanometers to micrometers. The sonication time and amplitude can be optimized for formulating particles with a diameter of, e.g., 0.1 to 300 μm.

In another embodiment, the aforementioned particle formulation can be used to generate a library of particles containing various composition, and different properties including, but not limited to size, charge, hydrophobicity, type and amount of targeting molecules.

Methods of Using Particles

The invention further comprises preparations, formulations, kits, and the like, comprising any of the compositions as described herein for use in various therapeutic and diagnostic methods. In some cases, treatment of a disease (e.g., cancer) can involve the use of compositions or "agents" as described herein. That is, one aspect of the invention involves a series of compositions (e.g., pharmaceutical compositions) or agents useful for treatment of a disease (e.g., cancer or a tumor). These compositions can also be packaged in kits, optionally including instructions for use of the composition for the treatment of such conditions. These and other embodiments of the invention can also involve promotion of the treatment of a disease (e.g., cancer or tumor) according to any of the techniques and compositions and combinations of compositions described herein.

In some embodiments, compositions and methods of the invention can be used to reduce, inhibit, or prevent the growth of a tumor or cancer, and/or to reduce, inhibit, or prevent the metastasis of a tumor or cancer. In some embodiments, compositions of the invention can be used to shrink or destroy a cancer. It should be appreciated that compositions of the invention can be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof). In some embodiments, a composition of the invention can be administered to a patient who has undergone a treatment involving surgery, radiation, and/or chemotherapy. In certain embodiments, a composition of the invention can be administered chronically to prevent, or reduce the risk of, a cancer recurrence.

In certain embodiments, the compositions disclosed herein can be used for delivery of nucleic acids, e.g., for exogenous gene expression or inhibition of gene expression. Due to their polyanionic and macromolecular characteristics, naked nucleic acids cannot freely cross cellular membranes, and thus require delivery vehicles to facilitate their intracellular uptake and endosomal escape, as well as to protect them from degradation during circulation. Cationic polymer and lipid-based nanocarriers are two current nucleic acid delivery systems. The disclosed particles combine the unique characteristics of polymeric vectors and liposomes together for more efficient nucleic acid delivery.

The compositions disclosed herein can also be used to deliver of immunomodulatory agents (e.g., antigens) and/or one or more immunostimulatory agents (e.g., adjuvants), e.g., for vaccination of subjects. Such compositions can be used in the treatment or prevention of a disorder, e.g., a disorder associated with an antigen present in the composition.

The compositions and methods of the invention are also useful for treating cancer by stimulating an antigen-specific immune response against a cancer antigen. A "tumor antigen" as used herein is a compound, such as a peptide, associated with a tumor or cancer and which is capable of provoking an immune response. In particular, the compound is capable of provoking an immune response when presented in the context of an MHC molecule. Tumor antigens can be prepared from cancer cells either by preparing crude extracts of cancer cells, for example, as described in Cohen, et al., Cancer Research, 54:1055 (1994), by partially purifying the antigens, by recombinant technology or by de novo synthesis of known antigens. Tumor antigens include antigens that are antigenic portions of or are a whole tumor or cancer polypeptide. Such antigens can be isolated or prepared recombinantly or by any other means known in the art. Cancers or tumors that can be treated using the particles described herein include, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

Compositions comprising particles of the present invention, in some embodiments, can be combined with pharmaceutically acceptable carriers to form a pharmaceutical composition, according to another aspect of the invention. As would be appreciated by one of skill in this art, the carriers can be chosen based on the route of administration as described below, the location of the target issue, the drug being delivered, the time course of delivery of the drug, etc.

A "pharmaceutical composition" or "pharmaceutically acceptable" composition, as used herein, comprises a therapeutically effective amount of one or more of the compositions described herein, formulated together with one or more pharmaceutically acceptable carriers (additives) and/or diluents. As described in detail, the pharmaceutical compositions of the present invention can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compositions of the present invention can be given in dosages, generally, at the maximum amount while avoiding or minimizing any potentially detrimental side effects. The compositions can be administered in effective amounts, alone or in a cocktail with other compounds, for example, other compounds that can be used to treat a disease. An effective amount is generally an amount sufficient to inhibit the disease within the subject.

One of skill in the art can determine what an effective amount of the composition is by screening the composition using known methods. The effective amounts may depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this invention can be varied so as to obtain an amount of the active ingredient that is effective to achieve the desired therapeutic response for a particular patient, composition, and mode of administration, without being toxic to the patient.

The selected dosage level may depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. For example, chronic treatments can involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above.

If desired, the effective daily dose of the active compound can be administered as two, three, four, five, six or more sub-doses administered separately at appropriate intervals throughout the day, optionally, in unit dosage forms.

While it is possible for a composition of the present invention to be administered alone, it can be administered as a pharmaceutical formulation (composition) as described above.

The compositions of the invention, in some embodiments, can be promoted for treatment of abnormal cell proliferation, diseases (e.g., cancers), or tumors, or includes instructions for treatment of accompany cell proliferation, cancers, or tumors, as mentioned above. In another aspect, the invention provides a method involving promoting the prevention or treatment of a disease (e.g., cancer) via administration of any one of the compositions of the present invention in which the composition is able to treat the disease. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition.

The kits described herein can also contain one or more containers, which can contain compounds such as the species, signaling entities, biomolecules and/or particles as described. The kits also can contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit can be provided as any suitable form, for example, as liquid solutions or as dried powders. When the composition provided is a dry powder, the powder can be reconstituted by the addition of a suitable solvent, which can also be provided. In embodiments where liquid forms of the composition are sued, the liquid form can be concentrated or ready to use. The solvent can depend on the compound and the mode of use or administration. Suitable solvents for drug compositions are well known and are available in the literature.

The kit, in one set of embodiments, can comprise a carrier means being compartmentalized to receive in close confinement one or more container means such as vials, tubes, and the like, each of the container means comprising a specific composition. Additionally, the kit can include containers for other components, for example, buffers useful in the assay.

As used herein, a "subject" or a "patient" refers to any mammal (e.g., a human), such as a mammal that may be susceptible to a disease (e.g., cancer). Examples include a human, a non-human primate, a cow, a horse, a pig, a sheep, a goat, a dog, a cat, or a rodent such as a mouse, a rat, a hamster, or a guinea pig. A subject can be a subject diagnosed with the disease or otherwise known to have the disease (e.g., cancer). In some embodiments, a subject can be diagnosed as, or known to be, at risk of developing a disease. In certain embodiments, a subject can be selected for treatment on the basis of a known disease in the subject. In some embodiments, a subject can be selected for treatment on the basis of a suspected disease in the subject. In some embodiments, a disease can be diagnosed by detecting a mutation associate in a biological sample (e.g., urine, sputum, whole blood, serum, stool, etc., or any combination thereof. Accordingly, a compound or composition of the invention can be administered to a subject based, at least in part, on the fact that a mutation is detected in at least one sample (e.g., biopsy sample or any other biological sample) obtained from the subject. In some embodiments, a cancer can not have been detected or located in the subject, but the presence of a mutation associated with a cancer in at least one biological sample can be sufficient to prescribe or administer one or more compositions of the invention to the subject. In some embodiments, the composition can be administered to prevent the development of a disease such as cancer. However, in some embodiments, the presence of an existing disease can be suspected, but not yet identified, and a composition of the invention can be administered to prevent further growth or development of the disease.

It should be appreciated that any suitable technique can be used to identify or detect mutation and/or over-expression associated with a disease such as cancer. For example, nucleic acid detection techniques (e.g., sequencing, hybridization, etc.) or peptide detection techniques (e.g., sequencing, antibody-based detection, etc.) can be used. In some embodiments, other techniques can be used to detect or infer the presence of a cancer (e.g., histology, etc.). The presence of a cancer can be detected or inferred by detecting a mutation, over-expression, amplification, or any combination thereof at one or more other loci associated with a signaling pathway of a cancer.

EXAMPLES

Example 1

Preparation and Characterization of Lipid-Polymer-Lipid Nanoparticles siRNA-encapsulated lipid-polymer-lipid nanoparticles were formed by a modified double-emulsion method. In brief, 3 mg ester-terminated poly(D,L-lactic-co-glycolic acid) (PLGA, Mw=50 kD, viscosity of 0.26-0.54 dL/g) (Durect Corporation, Pelham, Ala.) and 0.2 mg 1,2-dimyristoleoyl-sn-glycero-3-ethylphosphocholine (Tf salt) (EPC14:1, MW=852 D) (Avanti, Alabaster, Ala.) were dissolved in 1 mL dichloromethane (DCM) solvent. The siRNA solution was added dropwise into the EPC14:1 and PLGA solution and emulsified by probe sonication for about 25 seconds at a power of 10 watts to form a first emulsion. Next, the emulsified mixture was added into a 2 mL aqueous solution containing 5 μg/mL 1,2-distearoyl-sn-glycero-3-phosphoethanolamine-N-[methoxy(polyethylene glycol)-2000] (DSPE-PEG-OCH3) (Avanti, Alabaster, Ala.) and 1.25 μg/mL soybean lecithin (Alfa Aesar, Ward Hill, Mass.), followed by probe sonication for about 25 seconds at a 10 watts to form a double emulsion. The final double emulsion solution was poured into a beaker containing DSPE-PEG-OCH3/lecithin aqueous solution and stirred for 3 hours to allow the DCM solvent to evaporate and the particles to harden. The remaining organic solvent and free molecules were removed by washing the particle solution three times using an Amicon Ultra-4 centrifugal filter (Millipore, Billerica, Mass.) with a molecular weight cutoff of 100 kDa. The NP solution was finally concentrated in 1 mL phosphate buffered saline (PBS, Hyclone).

The nanoparticle structure was characterized by transmission electron microscopy (Tecnai™ G$^2$ Spirit BioTWIN, FEI Company, Hillsboro, Oreg.) operating at 80 kV. The TEM sample was prepared by adding NP droplets (10 μL, 3 mg/mL) onto a hydrophilized Formvar-coated copper grid (300-mesh) for 4 minutes. The grid was then washed with purified water one time and negatively stained with 1% uranyl acetate solution for 4 minutes. The stain solution was removed with a filter paper and air-dried prior to imaging. A representative micrograph is shown in FIG. 2A. The nanoparticles displayed a multi-layer morphology (see FIG. 2A, inset), with sizes ranging from about 100 to 300 nm.

Figure 2B:
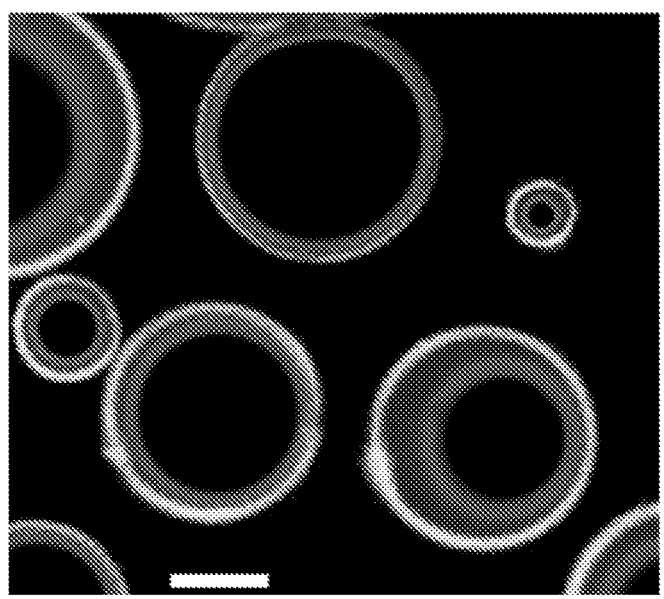

To examine the lipid-polymer-lipid structure, fluorescent dye-labeled particles with micrometer scales were prepared and visualized by laser scanning confocal fluorescence microscopy (Olympus Fluoview™ FV1000, Center Valley, Pa.) with 60× objective (oil N.A. 1.42). Particles were prepared as above, except that a hydrophobic dye (BODIPY® 665/676) and a Texas Red conjugated lipid (DHPE-Texas Red) were added into the organic solution containing PLGA and EPC14:1. In the DSPE-PEG-OCH3 and lecithin aqueous solution, DSPE-PEG-CF (carboxyfluorescein-conjugated DSPE-PEG) was co-dissolved. By using the modified double emulsion technique as described above, micronsize lipid-polymer-lipid particles could be formulated under different experimental parameters (low amplitude, short sonication time, and high PLGA concentration). Within the particles the BODIPY® 665/676 dye was co-localized with PLGA polymer due to its hydrophobicity, DHPE-Texas Red stayed in the inner layer together with cationic lipids, and DSPE-PEG-CF stained the outer PEG/lipid layer. The fluorescence emission spectra of the hydrophobic dye (ex/em 665/676 nm), DHPE-Texas Red (ex/em 595/615 nm), and DSPE-PEG-CF (ex/em 450/528 nm) were simultaneously detected in three confocal channels of Fluoview 1000 microscope. Three distinct layers were clearly seen in the majority of the particles (FIG. 2B).

Figure 3:
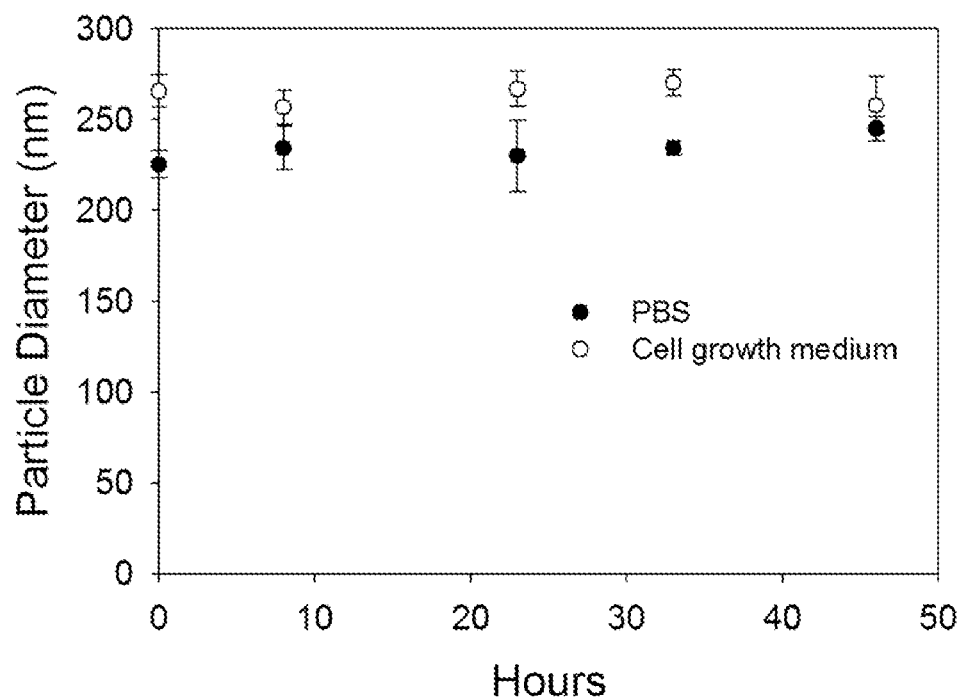
FIG. 3 is a chart showing particle size stability over 50 hours in PBS and cell growth medium.

NP size and surface charge (zeta potential) were determined by quasi-elastic laser light scattering with a ZetaPALS™ dynamic light scattering detector (15 mW laser, incident beam of 676 nm; Brookhaven Instruments Corporation, Holtsville, N.Y.) in PBS solution (6.7 mM $PO_4$ and 154 mM NaCl) and phosphate buffer solution (20 mM), respectively. The average particle diameter was around 225 nm, and the average zeta potential range was between −10 mV and 0 mV. NP size stability was tested by monitoring the size change of NPs in PBS and cell growth medium (DMEM supplemented with 10% FBS) over time at room temperature for 2 days. The size of the lipid-PLGA-lipid particles was relatively stable over the incubation period (FIG. 3).

Example 2 siRNA Encapsulation Efficiency and Release

Figure 4:
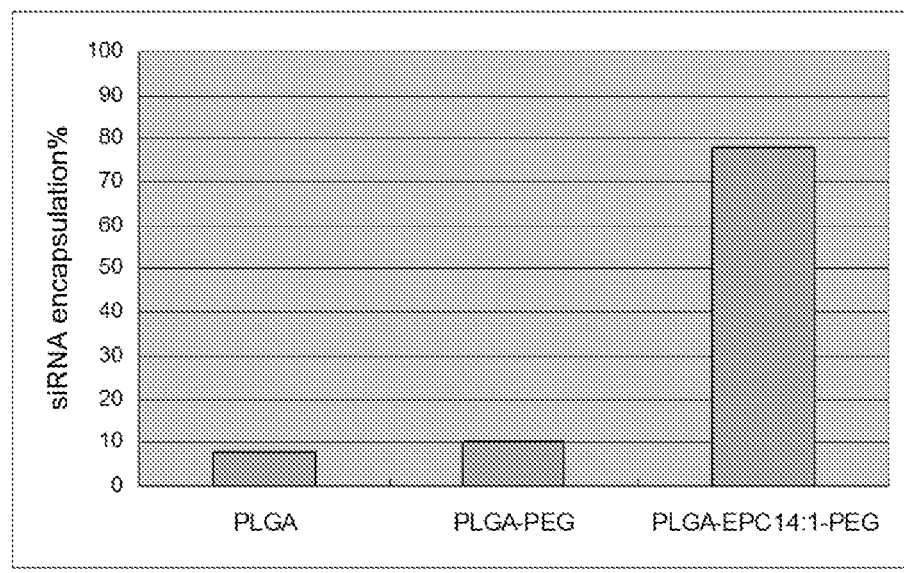
FIG. 4 is a bar graph depicting siRNA encapsulation efficiency of PLGA, PLGA-PEG, and PLGA-EPC14:1-PEG particles.

To determine loading and encapsulation efficiency, Cy3-labeled siRNA was encapsulated into the lipid-polymer-lipid particles, PLGA particles, and PLGA-PEG particles. Free siRNA was removed from the supernatant of the NP solutions, which were then centrifuged for 15 minutes at 13,200 rpm (16,100×g). The NP pellets were then resuspended in 1 mL PBS buffer. A standard curve correlating fluorescence and Cy3-siRNA concentration was used to determine the amount of siRNA encapsulated into the NPs. The fluorescence intensity was measured by Synergy HT multi-mode microplate reader (ex/em 530/590 nm, BioTek Instruments Inc., Winooski, Vt.). The lipid-polymer-lipid nanoparticles encapsulated nearly 80% of the input siRNA, whereas the PLGA and PLGA-PEG particles each encapsulated 10% or less of the input siRNA (FIG. 4).

Figure 5:
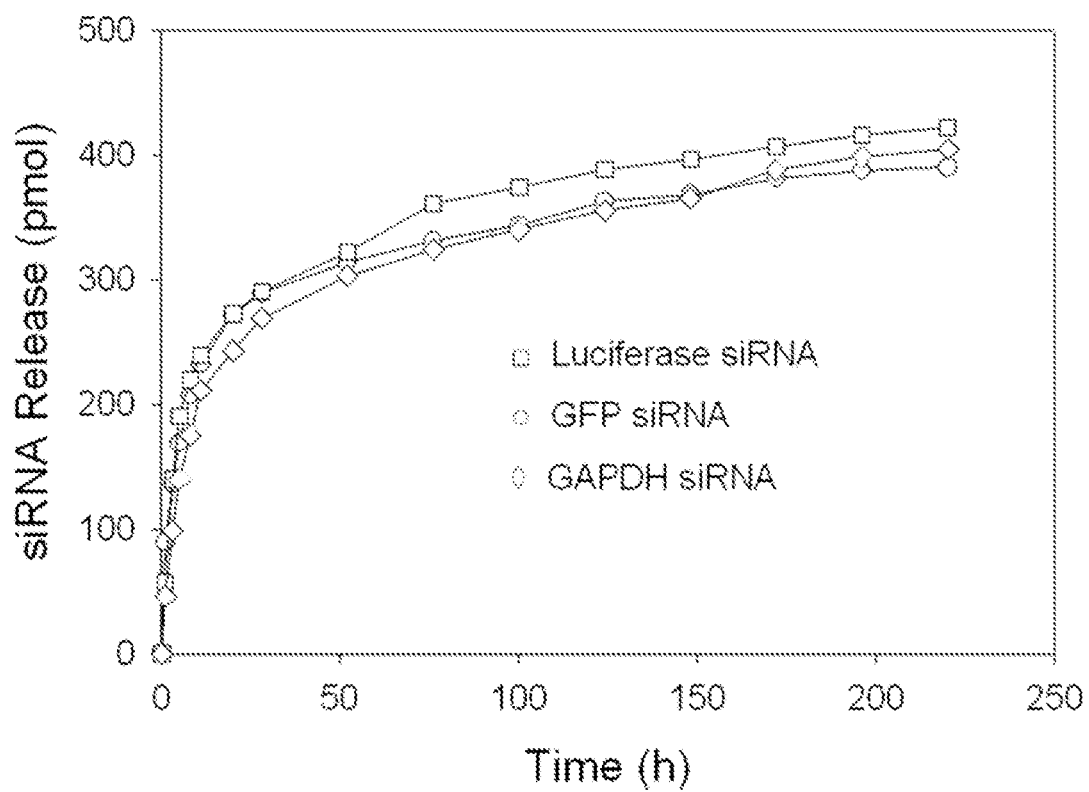
FIG. 5 is a line graph depicting siRNA release kinetics of nanoparticles encapsulating luciferase GL3 (square), GFP (circle), and GADPH (diamond) siRNA.

To measure siRNA release, lipid-polymer-lipid NPs (1.5 mg) with unlabeled luciferase [5'-CUU ACG CUG AGU ACU UCG AdTdT-3' (sense; SEQ ID NO:23) and 5'-UCG AAG UAC UCA GCG UAA GdTdT-3' (antisense; SEQ ID NO:24)], GFP [5'-GCA AGC UGA CCC UGA AGU UCA U-3' (sense; SEQ ID NO:25) and 5'-GAA CUU CAG GGU CAG CUU GCC G-3' (antisense; SEQ ID NO:26)], or GAPDH [5'-GUG GAU AUU GUU GCC AUC AdTdT-3' (sense; SEQ ID NO:27) and 5'-UGA UGG CAA CAA UAU CCA CdTdT-3' (antisense; SEQ ID NO:28)] siRNA were suspended in 1 mL PBS solution (pH 7.4), and incubated at 37° C. with gentle shaking. At each sampling time, the NP solution was centrifuged for 10 minutes at 13,200 rpm. The supernatant was removed for siRNA quantification, and an equal volume of PBS was replaced for continued monitoring of siRNA release. The siRNA in the supernatant was analyzed by using Quant-iT™ RiboGreen® assay (Molecular Probes, Eugene, Oreg.) according to the manufacturer's protocol. Release kinetics over 220 hours were similar for each of the three siRNAs (FIG. 5).

Example 3

In Vitro siRNA Transfection

Figure 6:
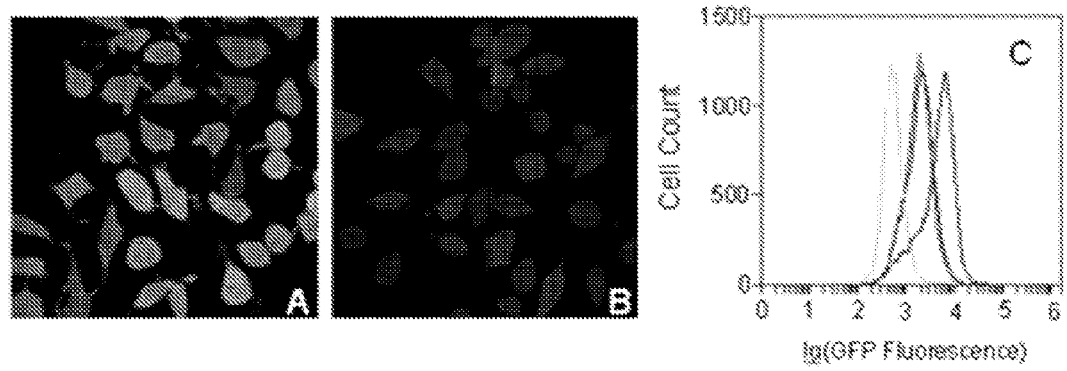
FIGS. 6A and 6B are laser scanning confocal fluorescence images of GFP expressed HeLa cells before (6A) and after (6B) incubation with NP(siRNA).
FIG. 6C is a set of flow cytometry histograms of GFP fluorescence of control HeLa cells (yellow), GFP expressed HeLa cells (black), GFP expressed HeLa cells treated with NP(GFP siRNA) (blue) and lipofectamine 2000(GFP siRNA) (red).

HeLa cells and GFP stably expressed HeLa (GFP-HeLa) cells were plated on 24-well plates (50,000 cells/well) in 1 mL growth medium [RPMI1640 medium (Invitrogen) supplemented with 10 v/v % fetal bovine serum and 1% v/v penicillin/streptomycin] and allowed to attach at 37° C. in a 5% $CO_2$ incubator for 24 hours. The cells were then transfected with naked GFP siRNA, NPs encapsulating GFP siRNA, NPs encapsulating negative control siRNA, and Lipofectamine 2000 encapsulating GFP siRNA. After 24 hours, the cells were washed with fresh growth medium and further incubated in the medium for one day. The transfected cell samples were then analyzed by Fluorescence Acquired Cell Sorting (FACS, Accuri C6 Flow Cytometer, Ann Arbor, Mich.). Cells were washed with PBS twice, treated with cell dissociation buffer (Invitrogen), transferred to microcentrifuge tubes, and pelletized for 5 minutes at 1000 rpm. Next, the cells were resuspended in PBS buffer containing propidium iodide (PI) which was used to determine the cell viability, and transferred to 5 mL polystyrene round-bottom tube with cell-strainer cap (BD Falcon). To obtain flow cytometry histogram and mean fluorescence intensity, a total of 20,000 cells were counted per transfection. The GFP expression after transfection was calculated via the shift in mean fluorescence from GFP-HeLa cells treated with NP(neg. siRNA) (positive control) to GFP-HeLa cells treated with NP(GFP siRNA). Untransfected HeLa cells without GFP expression were used as a negative control for autofluorescence. The nanoparticle encapsulated siRNA reduced GFP expression in the cells as efficiently as the lipofectamine siRNA, whereas the negative control siRNA was indistinguishable from the untransfected GFP-HeLa cells (FIG. 6C).

Figure 7:
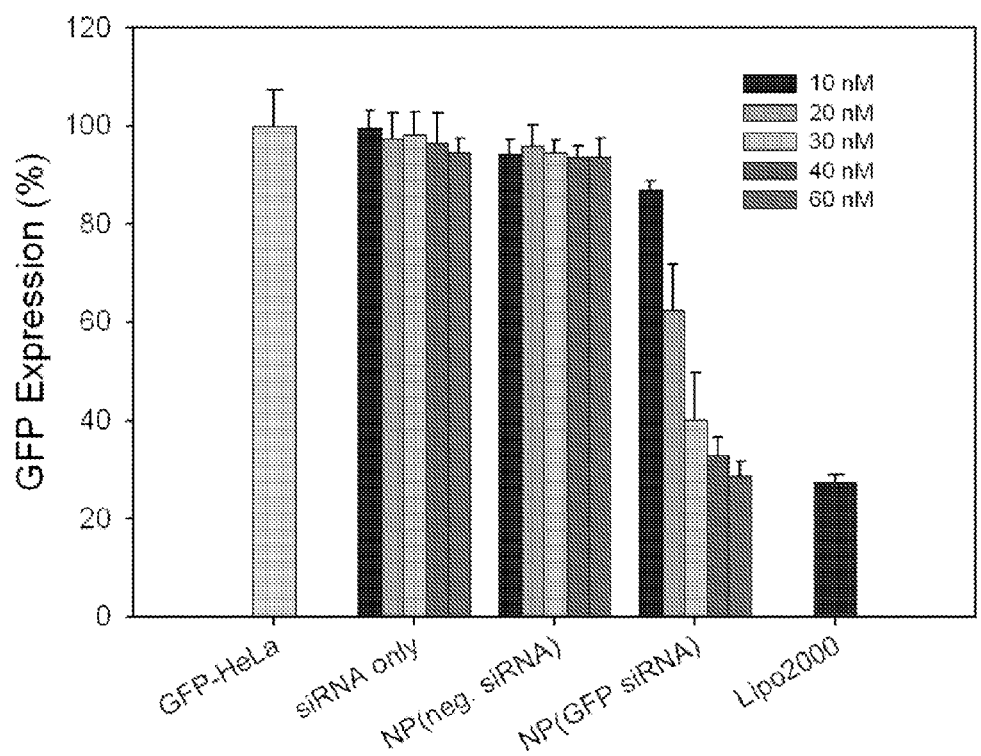
FIG. 7 is a bar graph depicting relative GFP expression for GFP-HeLa cells treated with the indicated amounts of naked siRNA [siRNA only], nanoparticles encapsulating a negative control siRNA [NP(negative siRNA)], nanoparticles encapsulating an siRNA specific for GFP [NP(siRNA)], and lipofectamine encapsulating an siRNA specific for GFP [Lipo2000].

The performance of naked siRNA, NP(neg. siRNA), and NP(GFP siRNA) was systemically tested as a function of siRNA dose. Naked siRNA and NP (neg. siRNA) showed little silencing under all conditions (FIG. 7). On the other hand, the GFP expression was gradually silenced with the increasing of GFP siRNA dose in NPs (FIG. 7). When 60 pmol (60 nM) siRNA was used, the NP(GFP siRNA) achieved ~72% GFP knockdown, comparable to the commercially available liposome-based lipoplex (Lipo2000-siRNA complex).

Figure 8:
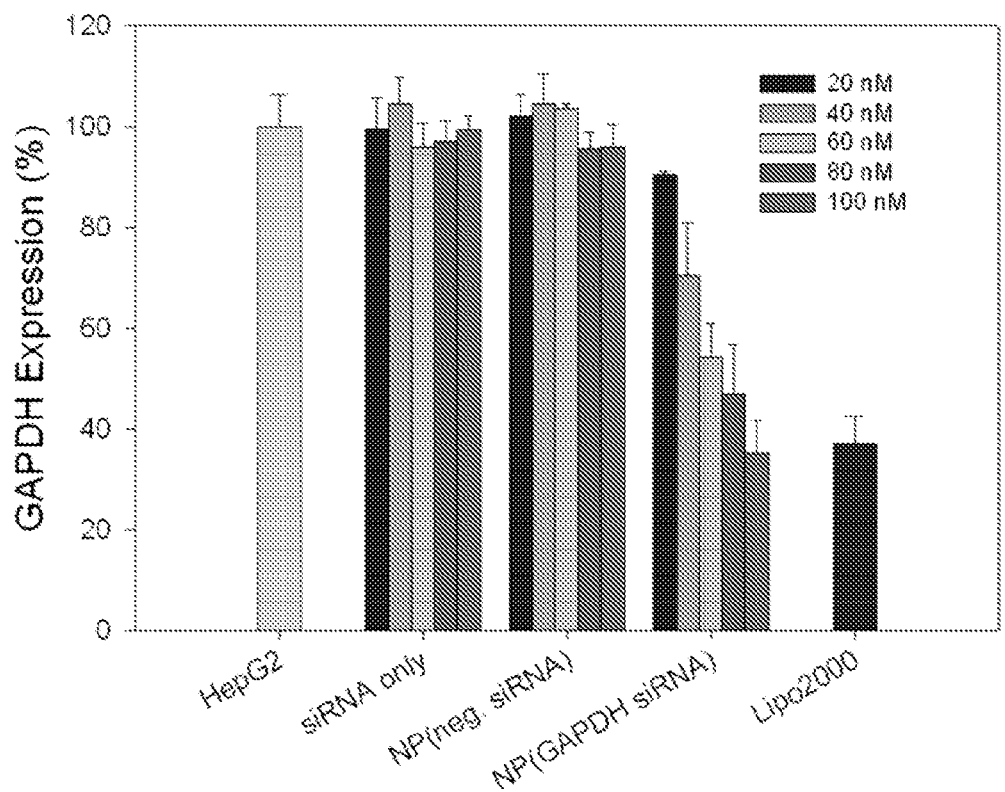
FIG. 8 is a bar graph depicting relative GADPH expression for HepG2 hepatocytes cells treated with the indicated amounts of naked siRNA [siRNA only], nanoparticles encapsulating a negative control siRNA [NP(negative siRNA)], nanoparticles encapsulating an siRNA specific for GADPH [NP(siRNA)], and lipofectamine encapsulating an siRNA specific for GADPH [Lipo2000].
Figure 9:
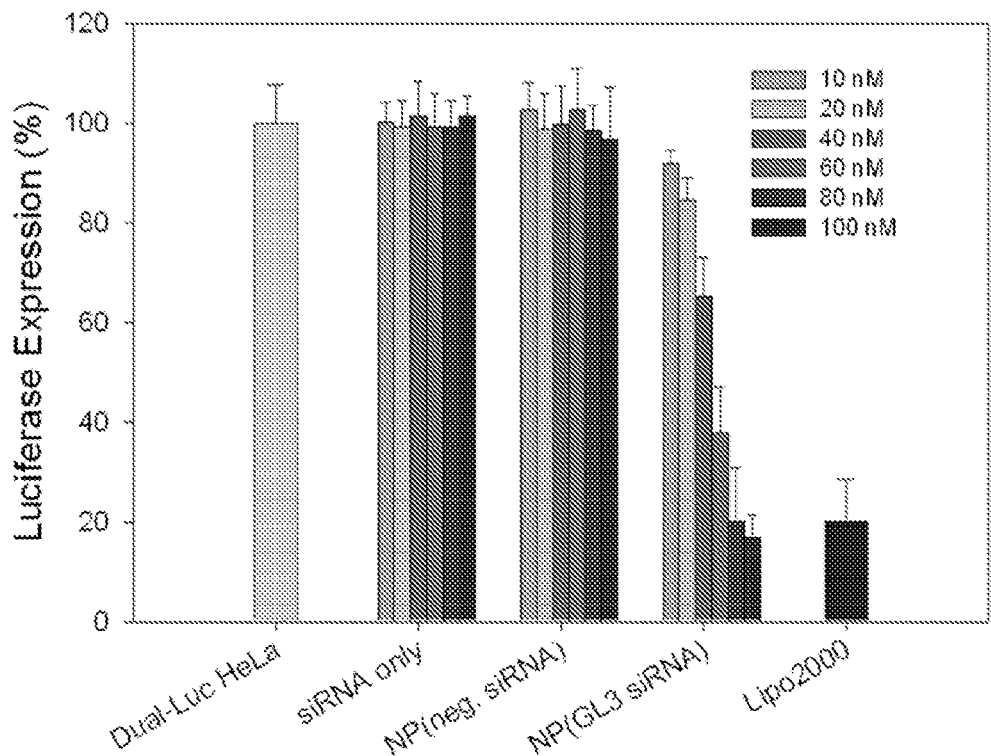
FIG. 9 is a bar graph depicting relative luciferase expression for luciferase-expressing HeLa cells treated with the indicated amounts of naked siRNA [siRNA only], nanoparticles encapsulating a negative control siRNA [NP(negative siRNA)], nanoparticles encapsulating an siRNA specific for luciferase [NP(siRNA)], and lipofectamine encapsulating an siRNA specific for luciferase [Lipo2000].

GFP-HeLa cells with and without siRNA transfection were also imaged by laser scanning confocal fluorescence microscopy. Cells were seeded on two 35 mm dishes with cover glass bottom (FluoroDish) in 2 mL growth medium for one day before transfection. One dish was then incubated with NP(neg. siRNA), and the other one with NP(GFP siRNA). Twenty-four hours post-transfection, both dishes were rinsed with fresh growth medium and subsequently incubated in the medium for one day. On the day of imaging, cells were washed twice with PBS, fixed with 4% formaldehyde, and mounted with non-fluorescent medium DAPI (Vector Laboratory, Inc. Burlingame, Calif.). Images were taken at around mid z-axis point of the cells. The GFP siRNA (FIG. 6A) clearly reduced GFP fluorescence relative to the control siRNA (FIG. 6B).

siRNA transfection of HepG2 hepatocytes and luciferase-expressing HeLa cells was conducted in 96-well plates (12,000 cells/well). The cells were allowed to adhere in 100 μL growth medium at 37° C. in a 5% $CO_2$ incubator overnight. After 24 hours of transfection followed by one day incubation, HepG2 hepatocytes were analyzed to measure the activity of GAPDH by using KDalert™ GAPDH Assay Kit. The expression of firefly and *Renilla* luciferase in HeLa cells was determined by Dual-Glo™ Luciferase Assay System. The fluorescence or luminescence intensity was measured by using a microplate reader (BioTek). FIGS. 8 and 9 show the response of GAPDH and firefly luciferase expression to siRNA in different formulations, respectively. Similar results were obtained in experiments as compared to the siRNA transfection of GFP-HeLa cells. Moreover, with the highest siRNA dose (10 pmol, or 100 nM), the gene knockdown efficiency of our NPs was better than that of Lipo2000. No significant toxicity was observed under all the conditions used for in vitro experiments. All of the in vitro transfection experiments were performed in quadruplicate.

Example 4

RNA Interference In Vivo

The effectiveness of the NP encapsulating siRNA to knock down expression in vivo was determined. Luciferase-expressing xenograft flank tumors were induced in 8-week-old BALB/C nude mice (Charles River Laboratories International, Inc. Wilmington, Mass.) by subcutaneous (s.c.) injection of $10^5$ Dual-Luc HeLa cells suspended in 1:1 media and matrigel. After ten days, GL3 siRNA, Lipo2000-GL3 siRNA complex, NP(GL3), and NP (neg. siRNA) were administrated into the tumor-bearing nude mice. The NP solution was concentrated to 15 mg/mL (PLGA concentration) with ~5.0 μM GL3 siRNA encapsulated. For preparing Lipo2000-siRNA complex, lipofectamine liposomes were mixed with DMEM growth medium for 5 minutes and subsequently mixed with siRNA for 30 minutes, according to the manufacturer's protocol. The final siRNA concentration in the lipoplex solution was the same as that in the NPs. The GL3 siRNA and its nano-complexes were directly injected into the tumor (~0.25 nmoles siRNA/50 mm³ tumor). Before dosing, the mice were monitored by a cryogenically cooled IVIS™ 100 Imaging System (Xenogen Corporation, Alameda, Calif.) using LivingImage™ acquisition and analysis software. Tumor bioluminescence images were then taken every 2 days. All of the in vivo imaging experiments were performed in quadruplicate.

Figure 10A:
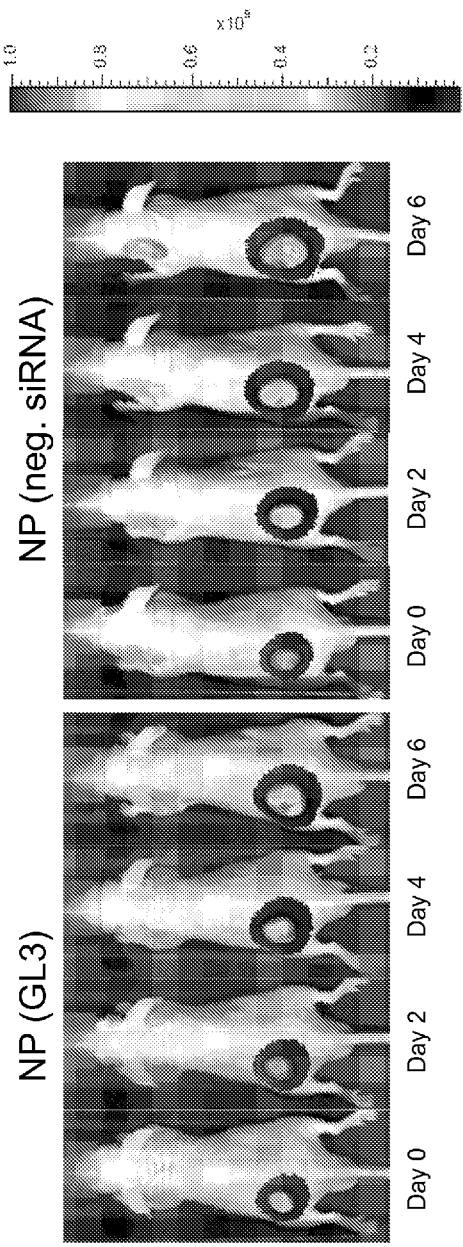
FIG. 10A is a set of images with overlayed luminescence of representative BALB/C nude mice bearing luciferase-expressing tumors on days 0, 2, 4, and 6 following injection with nanoparticles encapsulating siRNA specific for luciferase [NP(GL3)] or negative control siRNA [NP(neg. siRNA)]. Luminescence intensity is shown by the legend to the right.

After obtaining initial bioluminescence image of each mouse (day 0), four different treatments, GL3 siRNA, GL3 lipoplex, NP(neg. siRNA), and NP(GL3), were respectively administered into mice from each group by a single intra-tumoral injection. The mice bearing luciferase-expressing tumors were imaged every 2 days thereafter. Compared to the image at day 0, the bioluminescence intensity from the tumor treated with NP(GL3) was almost identical at day 2, and slightly increased at day 4 (FIG. 10A). On the other hand, the luciferase expression in the tumor of mice injected with NP(neg. siRNA) drastically increased in the following days, which was indicated by the enhancement of biolumi-nescence signal in FIG. 10A. These results suggest that the hybrid NPs are capable of delivering GL3 siRNA to inhibit luciferase expression in vivo.

Figure 10B:
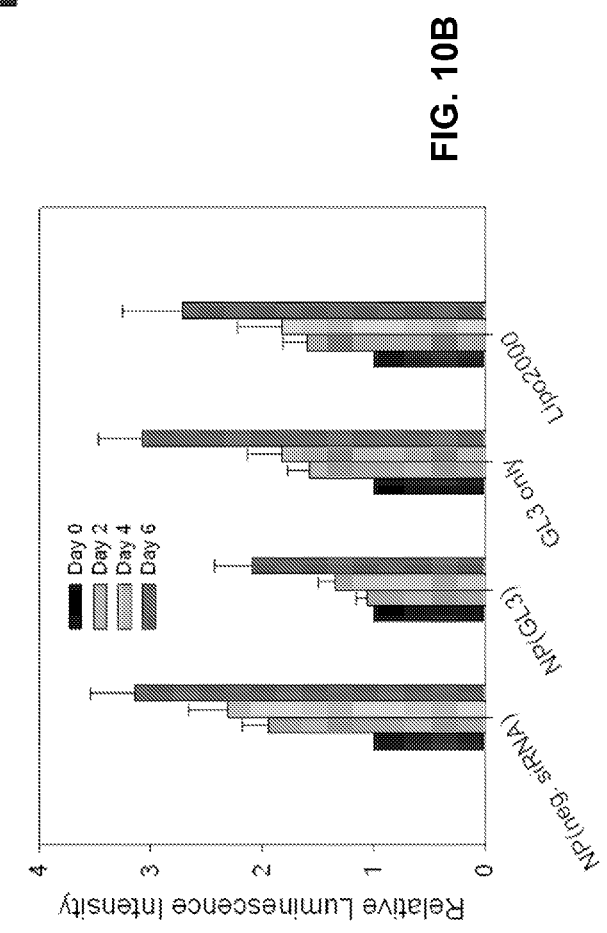
FIG. 10B is a chart depicting relative luminescence intensity of BALB/C nude mice bearing luciferase-expressing tumors on days 0, 2, 4, and 6 following injection with nanoparticles encapsulating negative control siRNA [NP (neg. siRNA)], nanoparticles encapsulating siRNA specific for luciferase [NP(GL3)], naked siRNA specific for luciferase [GL3 only], or lipofectamine encapsulating siRNA specific for luciferase [Lipo2000].

To quantitatively demonstrate the gene silencing efficacy of NP(GL3), relative to NP (neg. siRNA), the total biolu-minescence intensity (photon/sec) obtained from each tumor at different imaging dates was calibrated by normalizing the initial bioluminescence signal (at day 0) to equal 1. The relative luminescence intensity (n=4, mean±SE) was then plotted as a function of time (FIG. 10B). As can be seen, the luciferase expression is ~42-45% less in mice transfected with NP(GL3) than with NP(neg. siRNA), at day 2 and day 4. For comparison, mice treated with GL3 siRNA alone and GL3 lipoplex were also imaged, and the relative lumines-cence intensity was calculated. The change of luciferase expression in these two cases was similar to each other, indicating the cationic liposome did not provide obvious benefits for siRNA delivery during the in vivo experiments. Among the three regimens containing GL3 siRNA, the single injection of NP with siRNA decreased luminescence over the 6-day period more efficiently than the lipofectamine siRNA or naked siRNA. This example demonstrates that nanoparticle encapsulated siRNA can downregulate gene expression in vivo.

Example 5

Targeted Lipid-Polymer-Lipid Particle Formation

A targeting moiety (e.g., A10 RNA aptamer which binds to the Prostate Specific Membrane Antigen on the surface of prostate cancer cells) is conjugated to DSPE-PEG-COOH using EDC/NHS chemistry with a conjugate concentration of 0.7 mg/mL. Lipid-polymer-lipid nanoparticles are pre-pared as described in Example 1, except that 0.2 mg of the DSPE-PEG-Aptamer bioconjugate is mixed with 0.05 mg lecithin in 40 mL water as the solution for second emulsion. The nanoparticles are fabricated by using the same protocol aforementioned. This procedure yields nanoparticles tar-geted to prostate cancer cells expressing PSMA antigens.

Example 6

Drug-Drug Co-Delivery by Lipid-Polymer-Lipid NPs

By encapsulating hydrophilic drugs (e.g., doxorubicin) in the aqueous core and hydrophobic drugs (e.g., taxanes) in the polymer layer, lipid-polymer-lipid NPs can co-deliver two or more drugs simultaneously, maintaining the desired drug ratio for synergistic effects. To prepare such NPs, 0.5 mg/mL doxorubicin solution was added dropwise into the DCM solvent containing lipids and polymers essentially as described in Example 1, and also including 0.1 mg/mL paclitaxel. The mixture was emulsified by probe sonication to form first emulsion. The second emulsion and solvent evaporation were conducted essentially as described in Example 1. This procedure yields nanoparticles containing both doxorubicin and paclitaxel.

Example 7

Knockdown of Drug Resistance Proteins

Figure 12:
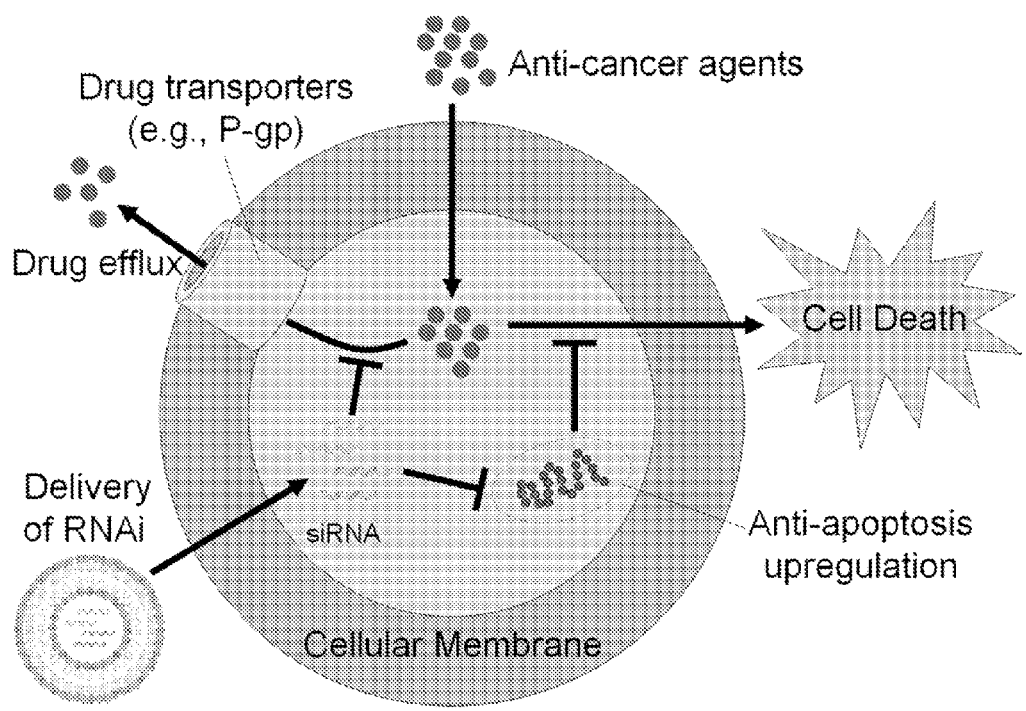
FIG. 12 is a schematic diagram of an exemplary strategy for increasing the efficacy of anti-cancer agents. siRNA targeting one or both of a drug transporter and an anti-apoptosis protein are delivered to a cell (e.g., a cancer cell) via a nanoparticle. The siRNA inhibit expression of drug transporters, increasing the effective concentration of anti-cancer agents in the cell, and also inhibit expression of anti-apoptosis proteins, leading to an increase in cell death.

The efficacy of chemotherapy in cancer treatment could be drastically limited by the development of multidrug resistance (MDR) in cancer cells. Among the various molecular mechanisms of drug resistance, the over-expres-sion of drug efflux transporters is considered the most common reason for MDR (FIG. 12). For example, P-glyco-protein (P-gp), the product of the MDR1 gene, is capable of effluxing out approximately 50% of currently used anti-cancer drugs, including anthracyclines and taxanes. Another main mechanism responsible for MDR is attributed to the inhibition of cell apoptosis by the over-expressed anti-apoptotic regulators such as Bcl-2 protein. Numerous efforts have so far been made to overcome MDR, including a new generation of drug analogs that are not P-gp substrates and the development of drug transporter inhibitors. Approaches are needed to address the significant obstacle of MDR in cancer chemotherapy.

Figure 13A:
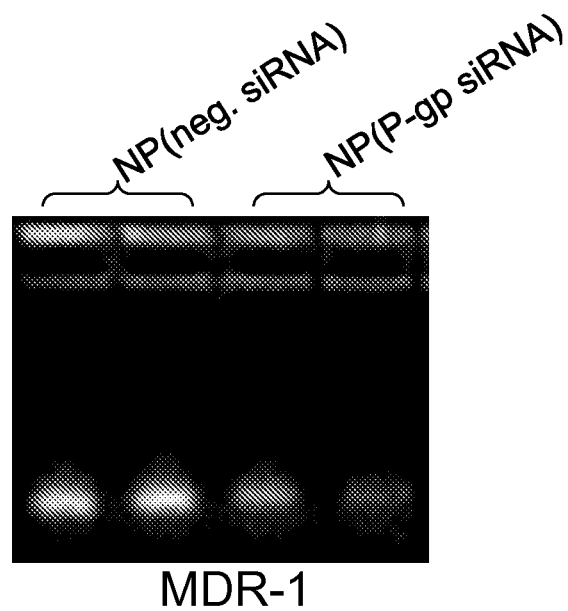
FIGS. 13A-13B are representative images of electrophoresis gels of the RT-PCR products for P-gp (13A) and control β-actin (13B) in paclitaxel-resistant A549 lung cancer cells after treatment with NP(neg. siRNA) and NP(P-gp siRNA).
Figure 13B:
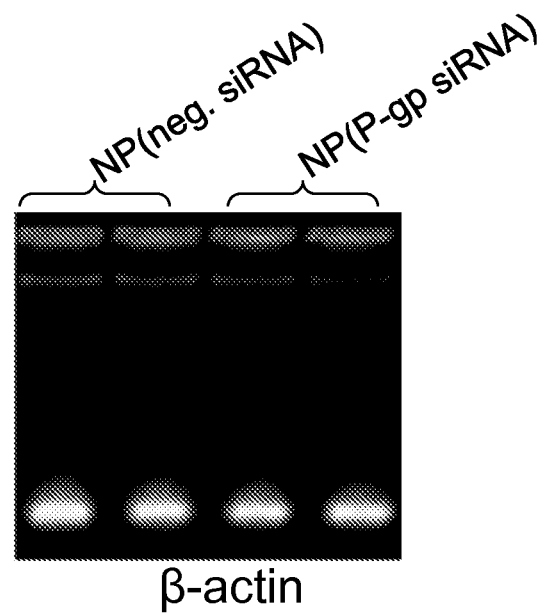

To test the efficacy of the lipid-polymer-lipid NPs in delivering siRNA to knockdown the over-expression of drug resistant genes (e.g., MDR1), paclitaxel-resistant lung cancer cells (A549TR) were used as a model. A549TR cells were plated on 12-well plates (100,000 cells/well) in 1 mL growth medium [F12K medium supplemented with 10 v/v % fetal bovine serum and 1% v/v penicillin/streptomycin] and allowed to attach at 37° C. in a 5% $CO_2$ incubator for 24 hours. The cells were then transfected with NPs encapsulating P-gp siRNA and NPs encapsulating negative control siRNA. After 24 hours, the cells were washed with fresh growth medium and further incubated in the medium for one day. Next, the cells were lysed and RNA molecules were extracted by RNeasy Microkit (Qiagen). The specific MDR1 gene (P-gp mRNA) and control Actin gene were then amplified by RT-PCR with the purified RNA. FIG. 13 shows that the expression of MDR-1 gene was greatly reduced when treated with NP(P-gp siRNA), as compared to NP(neg. siRNA); while the expression of control actin gene was not affected by NP(P-gp siRNA). This result demonstrates that the expression of drug resistant genes can be reduced by the siRNA-encapsulated lipid-polymer-lipid NPs.

Example 8 siRNA-Drug Co-Delivery by Lipid-Polymer-Lipid NPs for Drug Resistant Cancers

In the case of co-delivering chemotherapy and RNAi therapy to treat drug resistant cancers, a nanoparticle can encapsulate both an anti-cancer drug and siRNA with specific sequences reducing the expression of drug resistant transporters. Nanoparticles were prepared essentially as described in Example 1. In the first emulsion, 400 µL of 3.5 µM siRNA solution, which can suppress the over-expression of Bcl-2 protein, P-glycoprotein (P-gp), or other multidrug resistant-associated proteins in drug resistant cancer cells (Dong and Mumper, Nanomedicine, 5:597-615 (2010)), was added dropwise into the DCM solvent containing lipids, polymers, and the anti-cancer drug paclitaxel, and then emulsified by probe sonication for 25 seconds to form a first emulsion. The second emulsion and solvent evaporation were conducted essentially as described in Example 1. This procedure yielded nanoparticles containing both siRNA and anti-cancer drug for treating drug resistant cancers.

Figure 11:
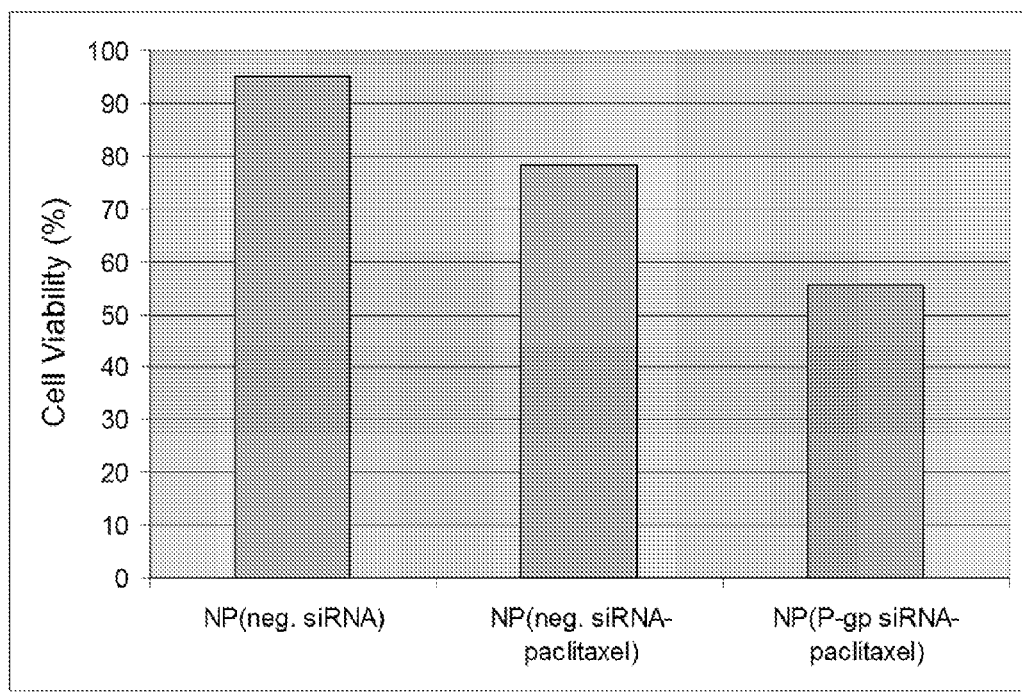
FIG. 11 is a bar graph depicting percent viability of paclitaxel-resistant A549 cells treated with nanoparticles containing a negative control siRNA [NP(neg. siRNA)], nanoparticles containing a negative control siRNA and paclitaxel [NP(neg. siRNA-paclitaxel)], and nanoparticles containing an siRNA targeting P-glycoprotein and paclitaxel [NP(P-gp siRNA-paclitaxel)].

To demonstrate the concept of co-delivering RNAi therapy and chemotherapy, the cellular cytotoxicity of nanoparticles containing a negative control siRNA [NP(neg. siRNA)], nanoparticles containing a negative control siRNA and paclitaxel [NP(neg. siRNA-paclitaxel)], and nanoparticles containing both an siRNA targeting P-glycoprotein and paclitaxel [NP(P-gp siRNA-paclitaxel)] was compared. Paclitaxel-resistant A549 cells were plated on 96-well plates (12,000 cells/well) in 1 mL growth medium [F-12K medium (ATCC) supplemented with 10 v/v % fetal bovine serum and 1% v/v penicillin/streptomycin] and allowed to attach at 37° C. in a 5% $CO_2$ incubator for 24 hours. The cells were then incubated with NP(neg. siRNA), NP(neg. siRNA-paclitaxel), and NP(P-gp siRNA-paclitaxel). After 24 hours, the cells were washed with fresh growth medium and further incubated in the medium for two days. The cellular cytotoxicity was then assessed using (3-(4,5-Dimethylthiazol-2-yl)-2,5-diphenyltetrazolium bromide (MTT) assay. The cell viability decreased from ~78% to ~56% in the presence of P-gp siRNA at the paclitaxel concentration of 800 nM (FIG. 11). This result indicates that administration of nanoparticles that deliver siRNA and drug simultaneously can be of particular use in treating drug resistant cancers.

Example 9

Theranostics Delivery by Lipid-Polymer-Lipid NPs

Targeted imaging and therapeutic agents can be combined within the same particle to allow visualization of sites of targeted drug delivery and deliver therapeutics simultaneously ("theranostics") (Debbage and Jaschke, 2008, Histochem. Cell Biol., 130:845-875). This technology can provide critical information on intracellular targets, ensure that therapeutic agents are efficiently reaching their target sites, and enable the effective early detection and treatment of diseases. By adding a solution or suspension of imaging agents (e.g., quantum dots) to the DCM solvent containing lipids, polymers, and drugs (e.g. paclitaxel, docetaxel, or PLA-doxorubicin), and emulsifying the mixture by probe sonication, a first emulsion is prepared. The second emulsion and solvent evaporation are conducted essentially as described in Example 1. This procedure yields lipid-polymer-lipid nanoparticles containing both drugs and imaging agents for theranostics.

Example 10

Nanoparticles for Vaccine Delivery

A nanoparticle vaccine contains immunomodulatory agents and immunostimulatory agents. The immunomodulatory agent, which induces an immune response in B and/or T cells, is encapsulated inside the particle and/or attached to the particle surface. The immunostimulatory agent, e.g., an adjuvant, is encapsulated in the polymer/lipid layer and/or in the inner aqueous core. Nanoparticles containing immunomodulatory and immunostimulatory agents are fabricated by using the same protocol above. To encapsulate immunomodulatory agents into the lipid-polymer-lipid nanocarrier, agent solutions (e.g., proteins and peptides) are added into DCM solvent containing polymer and lipid, and then emulsified by sonication. To attach the immunomodulatory agents to the particle surface, the agent is conjugated to the outer DSPE-PEG-COOH layer by EDC/NHS reaction. A hydrophobic or lipophilic immunostimulatory agent (e.g., TLR ligand R848) is mixed with polymer and lipid layer. A hydrophilic immunostimulatory agent (e.g., a CpG oligonucleotide) is encapsulated inside the inner aqueous core and/or adsorbed on the surface of the particle.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:
1. A particle comprising:
   an aqueous core;
   a first amphiphilic layer surrounding the aqueous core;
   a polymeric matrix surrounding the first amphiphilic layer; and
   one or more active agents, wherein at least one of the active agents is an immunostimulatory agent compris- ing a toll receptor (TLR) ligand ss/dsRNA, a polyI:C polynucleotide, or a CpG polynucleotide.

2. The particle of claim 1, further comprising a second amphiphilic layer surrounding the polymeric matrix.

3. The particle of claim 1, wherein the particle has an average diameter between about 40 nm and about 400 µm.

4. The particle of claim 1, wherein the first amphiphilic layer is a multilayer.

5. The particle of claim 1, wherein the first amphiphilic layer comprises naturally derived lipids, surfactants, or synthesized compounds with both hydrophilic and hydrophobic moieties.

6. The particle of claim 1, wherein the first amphiphilic layer comprises 1,2-dimyristoleoyl-sn-glycero-3-ethylphosphocholine (EPC14:1).

7. The particle of claim 1, wherein the first amphiphilic layer has a thickness of about 1 nm to about 50 nm.

8. The particle of claim 1, wherein the polymeric matrix comprises poly(lactide-co-glycolide) (PLGA), a polyalkylene glycol, or a polyester.

9. The particle of claim 1, wherein the polymeric matrix comprises polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof.

10. The particle of claim 8, wherein the polyester is poly(lactide-co-glycolide) (PLGA), polylactic acid, or polycaprolactone.

11. The particle of claim 1, wherein the polymeric matrix comprises a copolymer of two or more polymers.

12. The particle of claim 11, wherein the copolymer is a copolymer of poly(lactide-co-glycolide) (PLGA) and polyethylene glycol (PEG).

13. The particle of claim 1, wherein the polymeric matrix comprises a lipid-terminated polyalkylene glycol and a polyester or a polyethylene glycol (PEG) and poly(lactide-co-glycolide) (PLGA).

14. The particle of claim 1, wherein the polymeric matrix comprises a biodegradable polymer.

15. The particle of claim 2, wherein the second amphiphilic layer is a multilayer.

16. The particle of claim 2, wherein the second amphiphilic layer comprises lecithin.

17. The particle of claim 2, wherein the second amphiphilic layer has a thickness of about 1 nm to about 50 nm.

18. The particle of claim 1, further comprising a targeting agent.

19. The particle of claim 18, further comprising a second amphiphilic layer surrounding the polymeric matrix, and wherein the targeting agent is conjugated to a hydrophilic region of a molecule of the second amphiphilic layer.

20. The particle of claim 18, wherein the targeting agent comprises any one or more of a nucleic acid aptamer, polypeptide, protein ligand, small molecule, growth factor, hormone, cytokine, interleukin, antibody, antibody fragment, integrin, fibronectin receptor, carbohydrate, p-glycoprotein receptor, peptide, peptidomimetic, hydrocarbon, small modular immunopharmaceutical, cell binding sequence, affibody, nanobody, adnectin, domain antibody, or an avimer.

21. The particle of claim 1, further comprising an antigen associated with a surface of the particle.

22. The particle of claim 21, further comprising a second amphiphilic layer surrounding the polymeric matrix, and wherein the antigen is conjugated to a hydrophilic region of a molecule of the second amphiphilic layer.

23. The particle of claim 1, wherein at least one of the one or more the active agents is a therapeutic agent, immunomodulatory agent, diagnostic agent, biomolecule, bioactive agent, small molecule, drug, prodrug, protein, polypeptide, immunogen, hapten, or adjuvant.

24. A composition comprising a plurality of particles described in claim 1.

25. The composition of claim 24, wherein the plurality of particles has an average characteristic dimension of 500 nm or less.

26. A particle comprising:
an aqueous core;
a first amphiphilic layer surrounding the aqueous core, wherein the first amphiphilic layer comprises 1,2-dimyristoleoyl-sn-glycero-3-ethylphosphocholine (EPC14:1); and
a polymeric matrix surrounding the first amphiphilic layer.

27. The particle of claim 26, further comprising one or more active agents.

28. The particle of claim 27, wherein at least one of the active agents is an immunostimulatory agent.

29. The particle of claim 28, wherein the immunostimulatory agent is a toll receptor (TLR) ligand ss/dsRNA, polyI:C polynucleotide, or CpG polynucleotide.

30. The particle of claim 26, wherein the polymeric matrix comprises poly(lactide-co-glycolide) (PLGA), a polyalkylene glycol, or a polyester.

31. The particle of claim 1, wherein the immunostimulatory agent comprises a toll receptor (TLR) ligand ss/dsRNA.

32. The particle of claim 1, wherein the immunostimulatory agent comprises a polyI:C polynucleotide.

33. The particle of claim 1, wherein the immunostimulatory agent comprises a CpG polynucleotide.

* * * * *

UNITED STATES PATENT AND TRADEMARK OFFICE
CERTIFICATE OF CORRECTION

PATENT NO. : 9,549,901 B2  
APPLICATION NO. : 13/820351  
DATED : January 24, 2017  
INVENTOR(S) : Jinjun Shi et al.

Page 1 of 1

It is certified that error appears in the above-identified patent and that said Letters Patent is hereby corrected as shown below:

In the Claims

In Column 52, Line 23 (approx.), in Claim 24, after "particles" insert -- as --

Signed and Sealed this
Tenth Day of October, 2017

Joseph Matal
*Performing the Functions and Duties of the*
*Under Secretary of Commerce for Intellectual Property and*
*Director of the United States Patent and Trademark Office*